US008889107B2

(12) United States Patent
Schmidt et al.

(10) Patent No.: US 8,889,107 B2
(45) Date of Patent: Nov. 18, 2014

(54) NAIL VARNISH WITH A VELVETY FEEL

(75) Inventors: Ulrich Schmidt, Hersbruck (DE); Peter Kruger, Ludwigsfeld (DE); Michaela Gerstacker, Simmelsdorf (DE); Sonja Kurz, Neukirchen (DE); Barbara Mendler, Meersburg (DE)

(73) Assignee: Eckart GmbH, Hartenstein (DE)

( * ) Notice: Subject to any disclaimer, the term of this patent is extended or adjusted under 35 U.S.C. 154(b) by 58 days.

(21) Appl. No.: 13/575,153

(22) PCT Filed: Apr. 20, 2011

(86) PCT No.: PCT/EP2011/056386
§ 371 (c)(1),
(2), (4) Date: Jul. 25, 2012

(87) PCT Pub. No.: WO2012/022499
PCT Pub. Date: Feb. 23, 2012

(65) Prior Publication Data
US 2012/0294918 A1    Nov. 22, 2012

(30) Foreign Application Priority Data
Aug. 19, 2010  (EP) .................................... 10008669

(51) Int. Cl.
*A61Q 3/02*  (2006.01)
*A61Q 1/02*  (2006.01)
*A61K 8/81*  (2006.01)
*A61K 8/19*  (2006.01)

(52) U.S. Cl.
CPC ................ *A61Q 3/02* (2013.01); *A61K 8/8111* (2013.01); *A61K 8/19* (2013.01); *A61K 2800/436* (2013.01)

USPC ................................................ 424/61; 424/63

(58) Field of Classification Search
USPC .................... 424/63, 64, 70.08, 70.11, 66, 59
See application file for complete search history.

(56) References Cited

U.S. PATENT DOCUMENTS

| 3,407,160 A | 10/1968 | Frank |
| 3,864,294 A | 2/1975 | Busch, Jr. |
| 4,407,310 A | 10/1983 | Jadow |
| 4,822,423 A | 4/1989 | Soyama et al. |
| 5,330,750 A | 7/1994 | Sheard et al. |

(Continued)

FOREIGN PATENT DOCUMENTS

| DE | 2345560 | 5/1974 |
| DE | 102009037932 A1 | 2/2011 |

(Continued)

OTHER PUBLICATIONS

Freedictionary.com (term—"micronized", last visit Oct. 31, 2013).*

(Continued)

*Primary Examiner* — Ernst V Arnold
*Assistant Examiner* — Kyung Sook Chang
(74) *Attorney, Agent, or Firm* — The Webb Law Firm

(57) ABSTRACT

The present invention relates to a nail varnish including at least one effect pigment and at least one micronized wax, and to a process for producing it. Furthermore, the invention relates to the use of at least one micronized wax in a nail varnish and to an article provided with the nail varnish. Moreover, the invention relates to a mixture of at least one pigment and at least one micronized wax.

11 Claims, 10 Drawing Sheets

(56) References Cited

U.S. PATENT DOCUMENTS

| | | |
|---|---|---|
| 5,612,021 A | 3/1997 | Mellul |
| 5,964,936 A | 10/1999 | Reisser |
| 6,367,484 B1 | 4/2002 | Ramin et al. |
| 6,645,286 B2 | 11/2003 | Ostertag et al. |
| 6,818,051 B2 | 11/2004 | Anselmann et al. |
| 7,582,285 B2 | 9/2009 | Kruger et al. |
| 7,651,562 B2 | 1/2010 | Kaupp et al. |
| 7,828,890 B2 | 11/2010 | Henglein et al. |
| 2007/0031361 A1* | 2/2007 | Herrmann et al. ......... 424/70.11 |
| 2007/0190000 A1 | 8/2007 | Arnaud et al. |
| 2007/0243149 A1 | 10/2007 | Hofacker et al. |
| 2009/0126316 A1 | 5/2009 | Ilekti et al. |
| 2010/0297045 A1 | 11/2010 | Kaupp et al. |
| 2011/0052804 A1 | 3/2011 | Banks |
| 2011/0177142 A1 | 7/2011 | Nolte et al. |
| 2011/0226161 A1 | 9/2011 | Schumacher et al. |
| 2011/0259243 A1 | 10/2011 | Schumacher et al. |
| 2011/0265689 A1 | 11/2011 | Schumacher et al. |
| 2011/0265690 A1 | 11/2011 | Schumacher et al. |

FOREIGN PATENT DOCUMENTS

| | | |
|---|---|---|
| DE | 102009037933 A1 | 2/2011 |
| DE | 102009037934 A1 | 2/2011 |
| DE | 102009037935 A1 | 2/2011 |
| EP | 0289240 A1 | 11/1988 |
| EP | 0479669 A1 | 4/1992 |
| EP | 0848735 B1 | 6/1998 |
| EP | 1251152 B1 | 10/2002 |
| EP | 1532213 B1 | 5/2005 |
| EP | 1685198 B1 | 8/2006 |
| EP | 1758550 A2 | 3/2007 |
| EP | 1980594 B1 | 10/2008 |
| EP | 2217664 A1 | 8/2010 |
| JP | 63275512 A | 11/1988 |
| JP | 11302563 A | 11/1999 |
| WO | 0027347 A1 | 5/2000 |
| WO | 0188044 A1 | 11/2001 |
| WO | 2004056716 A1 | 7/2004 |
| WO | 2005063637 A1 | 7/2005 |
| WO | 2007039832 A2 | 4/2007 |
| WO | 2007115675 A2 | 10/2007 |
| WO | 2009097517 A1 | 8/2009 |
| WO | 2009129909 A1 | 10/2009 |

OTHER PUBLICATIONS

Römpp Lexikon Lacke und Druckfarben [Römpp Lexikon paints and printing inks], Georg Thieme Verlag 1998, keywords Farbmittel, Farbstoffe, Pigmente [Colorants, Dyes, Pigments].

S. Schellenberger, M.Entenmann, A. Hennemann, P. Thometzek, Farbe und Lack, Apr. 2007, p. 130.

Waxes for Personal Care Applications, Nov. 1, 2007, XP002617147.

Positiviliste der Kosmetikverordnung (Verordnung (EG) Nr. 1223/2009, Anhang IV respectively Code of Federal Regulations Title 21, Part 73.

Regulation No. 1223 of 2009, Official Journal of Dec. 22, 2009, L342, p. 59, Annex IV.

Byk-Gardner, catalog "Qualitätskontrolle für Lacke und Kunststoffe [Quality control for coatings and plastics]" 2011/2012, pp. 16.

Byk-Gardner, catalog "Qualitätskontrolle für Lacke und Kunststoffe [Quality control for coatings and plastics]" 2011/2012, pp. 97/98.

BYK-Gardner, catalog "Qualitätskontrolle für Lacke und Kunststoffe [Quality control for coatings and plastics]" 2011/2012, pp. 15 and 16.

* cited by examiner

NAIL VARNISH WITH A VELVETY FEEL

BACKGROUND OF THE INVENTION

1. Field of the Invention

The present invention relates to a nail varnish which is characterized, following application and drying, by an extraordinary combination of haptic and optical properties, to a process for producing it, to the use of at least one micronized wax in a nail varnish, and to an article provided with the nail varnish. Furthermore, the invention relates to a mixture of at least one pigment and at least one micronized wax.

2. Description of Related Art

In order to be noticeable at all by the consumer among the large number of nail varnishes on offer, not only are nail varnishes demanded which follow the particular current trend colors, but also those which offer original, new types of or unique effects.

U.S. Pat. No. 4,822,423 discloses silicon dioxide as matting agent for a nail varnish. Silicon dioxide with a particle size of 0.01 to 30 µm is added here in an amount of 1 to 10% by weight to the nail varnish formulation in order to obtain a matt film of varnish on the nail.

According to US 2009/0126316 A1, WO 2007/039832 A2 or WO 2009/097517 A1, fingernails can be provided with a visible and/or feelable relief effect. In order to produce this relief effect, a coating made up of several layers has to be applied, with at least one layer having spherical particles or fibers.

(Artificial) fingernails with a relief effect can be obtained by the process described in U.S. Pat. No. 6,367,484 B1. For this purpose, the fingernail is firstly provided with a film-forming layer, onto which spherical or oval particles that are insoluble in said layer are applied. Besides providing the relief effect, these particles also give the fingernail a "soft feel" effect. For good hold of the spherical or oval particles, these can be fixed onto the first layer by means of a second film-forming layer. The spherical particles used are preferably glass beads. The process described is not only limited to fingernails, but can also be used on skin, lips or hair.

A further option of giving a cosmetic formulation, including a nail varnish, a "soft touch" effect can, as described in U.S. Pat. No. 5,612,021, be to add a fullerene or a mixture of fullerenes.

An artificial fingernail comprising granular materials, such as glass beads, salt or sugar, which impart a structured surface to the artificial fingernail is described in U.S. Pat. No. 4,407,310.

Nail varnishes comprising microbeads are known from WO 00/27347 A1. Depending on the diameter of the microbeads, a different appearance can be imparted to a fingernail painted with this nail varnish. Relatively fine microbeads serve for example to increase the shine (diameter: 1 to 12 µm) or can be used as filler for evening out unevennesses in the fingernail (diameter: 1 to 40 µm). Relatively large microbeads (diameter: 50 to 150 µm) can give a fingernail painted with this nail varnish structure or a matt appearance.

SUMMARY OF THE INVENTION

In some non-limiting embodiments, the present invention provides a nail varnish comprising at least one effect pigment and at least one micronized wax.

Also provided is a mixture comprising at least one pigment and at least one micronized wax in the ratio of 10 to 49% by weight of pigment to 51 to 90% by weight of micronized wax, in each case based on the total weight of the components pigment and micronized wax.

BRIEF DESCRIPTION OF THE DRAWINGS

The foregoing summary, as well as the following detailed description, will be better understood when read in conjunction with the appended drawings. In the drawings.

DETAILED DESCRIPTION

Figure 1:
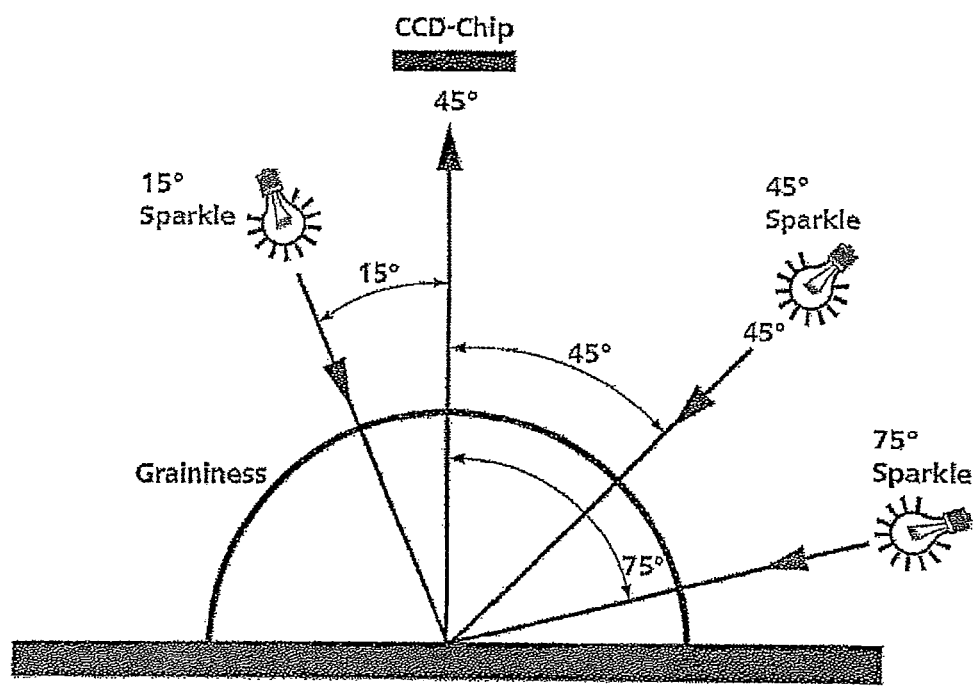
FIG. 1 is a diagram of Byk-mac effect measurement geometries (Byk-Gardner, catalog "Qualitäatskontrolle für Lacke and Kunststoffe [Quality Control for coatings and plastics]" 2011/2012, p. 97)

It is an object of the present invention to provide a nail varnish which is characterized, following application and drying, by an extraordinary combination of haptic and optical properties. The nail varnish is intended to impart a velvety feel to a(n) (artificial) fingernail painted therewith, which is perceived as being pleasant by the user. At the same time, an attractive optical appearance should be achieved.

The applied nail varnish should also have adequate mechanical stability and not be damaged merely by customary housework and/or office work. Moreover, the applied nail varnish should be retained in an optically attractive form for the longest possible period. It is also an object of the invention to provide a process for producing this nail varnish.

The object of the invention was achieved through the provision of a nail varnish comprising at least one effect pigment and also at least one micronized wax.

Preferred embodiments of the nail varnish according to the invention are given in dependent Claims 2 to 7.

The object was also achieved through the provision of a process for producing the nail varnish, where the process involves at least the following step: combining a nail varnish base, at least one micronized wax and at least one effect pigment to prepare a nail varnish.

Here, the order of addition is unimportant. Preferably, the components of the nail varnish according to the invention which are not soluble in the nail varnish base, micronized wax(es) and pigment(s) are added in succession or as a mixture to a nail varnish base that is colored with a soluble dye or is uncolored. In practice, it has proven useful to add platelet-like effect pigments to the nail varnish base in the last working step in order to largely avoid them from being damaged by any shear forces acting.

Furthermore, the invention provides the use of at least one micronized wax in a nail varnish. Preferred embodiments are given in dependent Claims 10 to 14.

Finally, the object of the invention is achieved through the provision of an article provided with the nail varnish according to the invention, the article being painted with one layer of the nail varnish. The article is preferably an artificial fingernail.

For the purposes of this invention, a fingernail is understood as meaning either a human fingernail or toenail or an artificial fingernail or toenail.

The inventors have surprisingly established that when using at least one micronized wax in a colorant-containing nail varnish, two effects are achieved simultaneously. Firstly, the nail varnish according to the invention has, following application and drying, a pleasant, velvety feel. This is very desirable if, for example, the painted fingernails and/or toenails come into contact with other areas of skin. Secondly, the addition of at least one micronized wax means that the nail varnish according to the invention imparts, following application and drying, to a(n) (artificial) fingernail painted therewith a matt, but not dull appearance. Furthermore, it has extraordinarily surprisingly been found that the optical sensory impression of the nail varnish according to the invention in the presence of at least one effect pigment following application and drying is less dependent on the viewing angle.

The nail varnish according to the invention can additionally comprise at least one colorant, which may either be a dye or a pigment. Dyes are black or colored substances which are soluble in the surrounding medium. Pigments are spherical or platelet-like colorants which, in contrast to dyes, are insoluble in the surrounding medium (cf. on this point DIN 55943: 2001-10 or Römpp Lexikon Lacke and Druckfarben [Römpp Lexikon paints and printing inks], Georg Thieme Verlag 1998, keywords Farbmittel, Farbstoffe, Pigmente [Colorants, Dyes, Pigments]). The pigments include both platelet-like effect pigments, such as metal effect pigments or pearlescent pigments, and also organic or inorganic pigments.

The colorants which can preferably be used in the nail varnish according to the invention can be selected inter alfa from the corresponding positive list of the Cosmetics Directive (Directive (EU) No. 1223/2009, Annex IV or Code of Federal Regulations Title 21, part 73).

In a preferred embodiment, the nail varnish according to the invention or the pigment/wax mixture according to the invention comprises at least one metal effect pigment.

The metal effect pigments which can be used in the nail varnish according to the invention or the pigment/wax mixture according to the invention can be produced either by conventional wet or dry grinding or by PVD processes.

Suitable metallic, optionally to be coated, platelet-like substrates can be selected from the group consisting of aluminum, copper, zinc, iron, titanium, stainless steel, gold, silver platelets, their alloys and their mixtures. Preferably, the metallic platelet-like substrates are selected from the group consisting of aluminum, copper, zinc, iron, stainless steel platelets, their alloys and their mixtures. Particularly preferably, the metallic platelet-like substrates are selected from the group consisting of aluminum, copper, zinc, iron platelets, their alloys and their mixtures. Very particularly preferably, the metallic substrates are selected from the group consisting of aluminum, copper, iron platelets, their alloys and their mixtures. Especially preferably, the metallic platelet-like substrates used are aluminum platelets, copper platelets, their alloys or their mixtures.

Metal effect pigments suitable specifically for use in nail varnishes are e.g. commercially available aluminum pigment dispersions such as Silverdream Moonlight 50 IL, Silverdream Starlight 70 IL, Metalure L-55350 AE or Metalure Prismatic H-50550 AE (Eckart) or commercially available stabilized platelet-like copper- or platelet-like copper/zinc alloys in the shades copper and gold bronze, such as, for example, Silverdream Bright Sunrise, Silverdream Bright Sunlight or Silverdream Bright Sunset (Eckart).

If the metallic platelet-like substrates are provided with at least one after-coating, this can be selected for example from metal oxides, metal oxide hydrates and/or metal hydroxides of titanium, aluminum, iron, cerium, chromium, silicon and/or mixtures thereof. Metal effect pigments coated with metal oxides are described for example in EP 1 532 213 B1 and in EP 1 758 550 A2. Metal effect pigments coated with silicon dioxide are available commercially, depending on the platelet-like metal or platelet-like metal alloy used as substrate, in the shades silver, gold bronze and copper under the trade name Visionaire (Eckart).

This color spectrum can be expanded by colored metal effect pigments. If aluminum platelets are oxidized by wet-chemical methods, as known for example from EP 0 848 735 B1, warm champagne shades can be achieved. The further coating of aluminum platelets, oxidized by wet-chemical methods, with, for example, iron oxides permits, according to EP 1 685 198 B1, intensive red shades. If the aluminum effect pigments are provided with a metal oxide layer comprising colored pigments, the colored pigments influence the appearance of the resulting aluminum effect pigment. Red or blue shades can be achieved, for example, using D & C Red 7 (CI 15 850), D & C Red 34 (CI 15 880), carmine (CI 75 470) or Prussian Blue (CI 77 400) as colored pigment. Colored aluminum effect pigments are commercially available for example under the trade name Visionaire (Eckart).

Magnetic metal effect pigments, such as, for example, platelet-like iron pigments, which can be stabilized with an inhibitor layer and/or anticorrosion layer, can also be used in the nail varnish according to the invention or the pigment/wax mixture according to the invention. Iron pigments of this kind are described for example in EP 1 251 152 B1 and are commercially available for example under the name Stapa WM Iron VP 401040 or Silverdream Polaris 90 WM (Eckart).

For cosmetic applications, the impurities of heavy metals present in the metal effect pigments, such as e.g. mercury, arsenic, lead, cadmium, should be as low as possible, preferably <70 ppm, based on the total weight of the metal effect pigment. Preferably, the mercury content should be ≤1 ppm, the arsenic content ≤5 ppm, the lead content ≤40 ppm and the cadmium content ≤15 ppm, in each case based on the total weight of the metal effect pigment.

Alternatively and/or additionally to the metal effect pigments, pearlescent pigments based on nonmetallic platelet-like substrates can be added to the nail varnish according to the invention or to the pigment/wax mixture according to the invention.

In a further preferred embodiment, the nail varnish according to the invention or the pigment/wax mixture according to the invention comprises at least one pearlescent pigment.

The nonmetallic, optionally to be coated, platelet-like substrates are preferably essentially transparent, preferably transparent, i.e. they are at least partially transparent for visible light.

The nonmetallic platelet-like substrates can be selected from the group consisting of natural mica platelets, synthetic mica platelets, glass platelets, $SiO_2$ platelets, $Al_2O_3$ platelets, BiOCl platelets, $TiO_2$ platelets, $Fe_2O_3$ platelets, sericite platelets, kaolin platelets, graphite platelets, talc platelets, polymer platelets, platelet-like substrates which include an inorganic-organic mixed layer. Furthermore, glass platelets which are coated on both sides with semi-transparent metal layers selected from the group consisting of silver, aluminum, chromium, nickel, gold, platinum, palladium, copper, zinc, titanium, alloys thereof and mixtures thereof can be used as nonmetallic platelet-like substrates. According to the invention, pearlescent pigments which can be used are also those whose substrates are mixtures of the platelet-like substrates given above.

Preferably, the nonmetallic platelet-like substrates are selected from the group consisting of natural mica platelets, synthetic mica platelets, glass platelets, $SiO_2$ platelets, $Al_2O_3$ platelets and mixtures thereof. The nonmetallic platelet-like substrates are particularly preferably selected from the group consisting of natural mica platelets, synthetic mica platelets, glass platelets and mixtures thereof. Very particularly preferred as substrates are glass platelets and synthetic mica platelets and mixtures thereof. In particular, platelet-like synthetic mica is preferred as substrate.

In contrast to synthetic platelet-like transparent substrates, natural mica platelets have the disadvantage that impurities can change the shade as a result of intercalated foreign ions, and that the surface is not ideally smooth as a result of production, but can have irregularities, such as e.g. steps.

Synthetic substrates such as, for example, glass platelets or synthetic mica platelets, by contrast, can have smooth surfaces and also a uniform thickness within an individual substrate particle, and also preferably over the entirety of all substrate particles. consequently, the surface offers only a few scattering centers for incident and/or reflected light and thus permits, after coating these platelet-like substrates, more shiny and more color intensive pearlescent pigments than using platelet-like natural mica as substrate. The glass platelets used are preferably those which are produced by the processes described in EP 0 289 240 A1, WO 2004/056716 A1 and WO 2005/063637 A1. The glass platelets that can be used as substrate can have, for example, a composition according to the teaching of EP 1 980 594 B1.

The difference described above between pearlescent pigments based on platelet-like transparent natural and synthetic substrates is also evident in nail varnish applications. Pearlescent pigments based on synthetic substrates usually impart a more color-pure and more shiny appearance to a nail varnish application.

The nonmetallic platelet-like substrate, as described above, can be provided with at least one layer or coating, where the at least one layer preferably comprises metal oxides, metal oxide hydrates, metal hydroxides, metal suboxides, metals, metal fluorides, metal oxyhalides, metal chalcogenides, metal nitrides, metal oxynitrides, metal sulfides, metal carbides or mixtures thereof. According to a preferred variant, the at least one layer or coating consists of the materials specified above.

Preferably used as the layer or coating are metal oxides, metal oxide hydrates, metal hydroxides and/or mixtures thereof. Particular preference is given to using metal oxides and metal oxide hydrates and/or mixtures thereof. Materials specified above can be present either as layers separated from one another separately or else alongside one another in the same layer.

The terms layer or coating are used interchangeably, unless stated otherwise.

The coating can either enclose the substrate entirely, be present only partially on the substrate or only cover its upper and/or lower surface.

The at least one layer can be an optically active layer and/or serve as a protective layer.

If a highly refractive layer is applied to a nonmetallic platelet-like substrate, then the refractive index is n≥1.8, preferably n≥1.9 and particularly preferably n≥2.0. In the case of a low-refractive layer or coating, the refractive index is n<1.8, preferably n<1.7 and particularly preferably n<1.6.

Suitable highly refractive layers are, for example, metal oxides such as titanium oxide, preferably titanium dioxide ($TiO_2$), iron oxide, preferably iron(III) oxide ($Fe_2O_3$) and/or iron(II/III) oxide ($Fe_3O_4$), zinc oxide, preferably ZnO, tin oxide, preferably tin dioxide ($SnO_2$), zirconium oxide, preferably zirconium dioxide ($ZrO_2$), antimony oxide, preferably antimony(III) oxide ($Sb_2O_3$), magnesium oxide, preferably MgO, cerium oxide, preferably cerium(IV) oxide ($CeO_2$) and/or cerium(III) oxide ($Ce_2O_3$), cobalt oxide, preferably cobalt(II) oxide (CoO) and/or cobalt(II/III) oxide ($Co_3O_4$), chromium oxide, preferably chromium(III) oxide ($Cr_2O_3$), copper oxide, preferably copper(I) oxide ($Cu_2O$) and/or copper(II) oxide (CuO), vanadium oxide, preferably vanadium (IV) oxide ($VO_2$) and/or vanadium(III) oxide ($V_2O_3$), metal sulfides such as zinc sulfide, preferably zinc(II) sulfide (ZnS), metal oxide hydrates such as goethite (FeOOH), titanates such as calcium titanate ($CaTiO_3$) or iron titanates, such as e.g. ilmenite ($FeTiO_3$), pseudobrookite ($Fe_2TiO_5$) and/or pseudorutile ($Fe_2Ti_3O_9$), metals, such as e.g. molybdenum, iron, tungsten, chromium, cobalt, nickel, silver, palladium, platinum, mixtures and/or alloys thereof, doped metal oxides, such as, for example, titanium dioxide and zirconium dioxide, which are colored with selectively absorbing colorants, and/ or mixtures thereof. The last-mentioned coloration of non-absorbing highly refractive metal oxides can take place e.g. by incorporating colorants into the metal oxide layer, by their doping with selectively absorbing metal cations or colored metal oxides such as iron(III) oxide or by coating the metal oxide layer with a film containing a colorant.

Preferably, the highly refractive layer comprises metal oxides, metal hydroxides and/or metal oxide hydrates. Particular preference is given to using metal oxides. Very particular preference is given to using titanium dioxide and/or iron oxide and also mixtures thereof.

If titanium dioxide is used for the coating, the titanium dioxide can be present in the rutile or anatase crystal modification. The rutile form can be obtained inter alia by, for example, applying a layer of tin dioxide to the platelet-like substrate to be coated prior to applying the titanium dioxide layer. On this layer of tin dioxide, titanium dioxide crystallizes in the rutile modification. The tin dioxide can be present here as a separate layer, where the layer thickness can be a few nanometers, for example less than 10 nm, further preferably less than 5 nm, even more preferably less than 3 nm. However, the tin dioxide can also be present with the titanium dioxide at least partially in a mixture.

Examples of low-refractive layers are inter alia metal oxides such as silicon oxide, preferably silicon dioxide ($SiO_2$), aluminum oxide, preferably aluminum(III) oxide ($Al_2O_3$), boron oxide, preferably boron(III) oxide ($B_2O_3$), metal fluorides such as magnesium fluoride, preferably $MgF_2$, aluminum fluoride, preferably $AiF_3$, cerium fluoride, preferably cerium(III) fluoride ($CeF_3$), calcium fluoride, preferably $CaF_2$, metal oxide hydrates such as aluminum oxide hydrate AiO(OH), silicon oxide hydrate, preferably $SiO_2 \cdot H_2O$ and/or mixtures thereof.

Preferably, the low-refractive layer comprises silicon dioxide.

If the nonmetallic platelet-like substrate is coated with only a single metal oxide layer, then this preferably has a high refractive index. Depending on the geometric metal oxide layer thickness, pearlescent pigments of this type can bring about different color effects, as shown in Table 1.

TABLE 1

Typical colors and geometric layer thicknesses of pearlescent pigments

| | Coating/geometric layer thickness | Color |
|---|---|---|
| Silver-white pearlescent pigments | $TiO_2$: 40-60 nm | silver |
| Interference pigments | $TiO_2$: 20-40 nm | pale blue |
| | $TiO_2$: 60-80 nm | yellow |
| | $TiO_2$: 80-100 nm | red |
| | $TiO_2$: 100-140 nm | blue |
| | $TiO_2$: 120-160 nm | green |
| | $TiO_2$: 280-320 nm | green (III order) |

TABLE 1-continued

Typical colors and geometric layer thicknesses of pearlescent pigments

| | Coating/geometric layer thickness | Color |
|---|---|---|
| Color luster pigments | $Fe_2O_3$: 35-45 nm | bronze |
| | $Fe_2O_3$: 45-55 nm | copper |
| | $Fe_2O_3$: 55-65 nm | red |
| | $Fe_2O_3$: 65-75 nm | red-violet |
| | $Fe_2O_3$: 75-85 nm | red-green |
| | $Fe_3O_4$ | black |
| Combination pigments | $TiO_2/Fe_2O_3$ | gold shades |
| | $TiO_2/Cr_2O_3$ | green |
| | $TiO_2$/Prussian Blue | deep blue |

Pearlescent pigments coated with $TiO_2$ and/or iron oxide and based on platelet-like natural mica are commercially available for example under the name Prestige (Eckart). If the platelet-like transparent substrate consists of synthetic mica, pearlescent pigments of this type are commercially available e.g. under the trade name SynCrystal (Eckart). $Al_2O_3$ platelets coated with $TiO_2$ and/or iron oxide and correspondingly coated $SiO_2$ platelets are supplied for example under the trade name Timiron or Xirona (Merck). Glass platelets coated with $TiO_2$ and/or iron oxide are supplied e.g. under the name Mirage (Eckart), under the name Reflecks (BASF Catalysts) or under the name Ronastar (Merck).

Pearlescent pigments based on synthetic substrates and characterized by the characteristic data $D_{10}$, $D_{50}$ and $D_{90}$ from the cumulative frequency distribution of the volume-averaged size distribution function with a span $\Delta D = (D_{90} - D_{10})/D_{50}$ of 0.7 to 1.4 are characterized, according to EP 2 217 664 A1, by their high color purity.

If a color-neutral silver shade typical of aluminum pigments, the high coverage and the characteristic light/dark flop of a metal effect pigment is desired, but no metal effect pigment is to be used in the nail varnish according to the invention and/or the pigment/wax mixture according to the invention, then a silver-colored pigment with an ilmenite-containing layer based on a nonmetallic synthetic platelet-like substrate can be used.

The nonmetallic platelet-like substrates can also be coated with a multilayer layer structure with or consisting of metal oxide, metal hydroxide, metal suboxide and/or metal oxide hydrate, in which case the order of the layers can be variable. Preference is given here to a layer order in which at least one highly refractive layer and at least one low-refractive layer are arranged on a substrate in an alternating way. In the alternating arrangement, it is also possible to arrange one or more highly refractive layers directly one above the other and subsequently one or more low-refractive layers directly one above the other. However, it is essential that highly refractive layers and low-refractive layers occur in the layer structure. Preferably, starting from the platelet-like substrate, at least one highly refractive, low-refractive and again highly refractive layer are arranged, which results in pearlescent pigments with particularly intense interference colors. The interference color here can be silvery or non-silvery depending on the layer structure and layer thicknesses. Pearlescent pigments of this type are known for example from DE 10 2009 037 935 A1, DE 10 2009 037 934 A1, DE 10 2009 037 933 A1 or DE 10 2009 037 932 A1.

Moreover, pigments with an interference effect which do not have a substrate, e.g. liquid crystals such as helicones (LCP Technology) or particles with an opalescent effect, consisting of monodisperse beads in a three-dimensional, domain-wise tightly packed and regularly arranged structure, described for example in WO 2001/88044 A1, can also be used. Moreover, holographic glitter pigments, such as e.g. Geometric Pigments (Spectratek Tech), fluorescent pigments, phosphorescent pigments, photochromic pigments, thermochromic pigments and so-called "Quantum Dots" (Quantum Dot), can also be used in the nail varnish according to the invention and/or the pigment/wax mixture according to the invention.

In addition, "glitter" effect pigments, which are available for example under the trade name Metasomes Standard/Glitter in different colors (yellow, red, green, blue; Floratech), can also be used. The glitter particles here can be present in mixtures with different auxiliaries and colorants, such as, for example, the colorants with the Color Index (CI) numbers 19 140, 77 007, 77 289, 77 491.

Colorants which can be used in the nail varnish according to the invention and/or the pigment/wax mixture according to the invention are for example one or more substances from the following group: 2,4-dihydroxyazobenzene, 1-(2'-chloro-4'-nitro-1'-phenylazo)-2-hydroxynaphthalene, Ceres red, 2-(4-sulfo-1-naphthylazo)-1-naphthol-4-sulfonic acid, calcium salt of 2-hydroxy-1,2'-azonaphthalene-1'-sulfonic acid, calcium and barium salts of 1-(2-sulfo-4-methyl-1-phenylazo)-2-naphthylcarboxylic acid, calcium salt of 1-(2-sulfo-1-naphthylazo)-2-hydroxynaphthalene-3-carboxylic acid, aluminum salt of 1-(4-sulfo-1-phenylazo)-2-naphthol-6-sulfonic acid, aluminum salt of 1-(4-sulfo-1-naphthylazo)-2-naphthol-3,6-disulfonic acid, 1-(4-sulfo-1-naphthylazo)-2-naphthol-6,8-disulfonic acid, aluminum and zirconium salts of 4,5-dibromofluorescein, aluminum and zirconium salts of 2,4,5,7-tetrabromofluorescein, aluminum salt of 3',4',5',6'-tetrachloro-2,4,5,7-tetrabromofluorescein, aluminum salt of 2,4,5,7-tetraiodofluorescein, aluminum salt of quinophthalonedisulfonic acid, aluminum salt of indigodisulfonic acid. It is also possible to use natural dyes, such as e.g. paprika extract, β-carotene or cochineal.

Suitable organic pigments for use in the nail varnishes according to the invention and/or the piyment/wax mixtures according to the invention include, for example, nitroso, nitro, azo, xanthene, quinoline, anthraquinone, phthalocyanine, metal complex, isoindolinone, isoindoline, quinacridone, perinone, perylene, diketopyrrolopyrrole, thioindigo, dioxazine, triphenylmethane and quinophthalone compounds. Furthermore, the organic pigments can for example be selected from carmines, carbon black, aniline black, quinacridone, phthalocyanine blue, D & C Red 21 (CI 45 380), D & C Orange 5 (CI 45 370), D & C Red 27 (CI 45 410), D & C Orange 10 (CI 45 425), D & C Red 3 (CI 45 430), D & C Red 7 (CI 15 850), D & C Red 4 (CI 15 510), D & C Red 33 (CI 17 200), D & C Red 34 (CI 15 880), D & C Yellow 5 (CI 19 140), D & C Yellow 6 (CI 15 985), D & C Yellow 10 (CI 77 002), D & C Green 3 (CI 42 053), D & C Green 5 (CI 61 570) and/or D & C Blue 1 (CI 42 090).

Suitable inorganic pigments include, for example, metal oxides and/or other metal compounds that are sparingly soluble or insoluble in water, in particular metal oxides of titanium, for example titanium dioxide (CI 77891), zinc, iron, for example red and black iron oxide (CI 77491 (red), 77499 (black)) or iron oxide hydrate (CI 77492, yellow), zirconium, silicon, manganese, aluminum, cerium, chromium, and also mixed oxides of said metals and mixtures thereof. Further suitable inorganic pigments are, for example, barium sulfate, zinc sulfide, manganese violet, ultramarine blue and/or Prussian Blue pigments.

The organic and inorganic colored pigments are generally ground in a bead mill or grinding-body mill, e.g. using zirconium oxide beads. The grinding can take place in an organic solvent, for example in paraffin oil or isopropanol. In terms of the compatibility with standard commercial nail varnish systems, isopropanol is preferred.

The pigments can be surface-modified, in which case, for example, a hydrophilic, amphiphilic or hydrophobic character is formed and/or is to be retained. This surface treatment can consist in providing the pigments with a thin hydrophilic and/or hydrophobic inorganic and/or organic layer by processes known to the person skilled in the art.

The nail varnish according to the invention or the pigment/wax mixture according to the invention comprises at least one micronized wax as well as at least one colorant. Micronized waxes or microwaxes are lipophilic compounds, preferably with an average particle size $D_{50}$ from a range from 2.5 to 91 μm, further preferably from a range from 3 to 79 μm, even more preferably from a range from 4 to 69 μm, particularly preferably from a range from 5 to 59 μm and very particularly preferably from a range from 6 to 49 μm. Furthermore, it has been found that micronized waxes with an average particle size $D_{50}$ from a range from 8 to 22 μm are particularly suitable. The micronized waxes are preferably present as discrete individual wax particles, although they may also be aggregates with an identical average particle size $D_{50}$.

Moreover, the micronized wax has preferably only a few, preferably no, particles in the size range >200 μm since otherwise the described optical and haptic effect can no longer be retained in the applied and dried nail varnish. The human eye can clearly see particles with a size of >200 μm, meaning that the image seen by a viewer of the applied and dried nail varnish is not homogeneous. In the worst case, such coarse wax particles are perceived as incorrect coating, i.e. as undesired raised areas in the varnish film. In terms of feel, wax particles with a particle diameter of >200 μm are also perceived as unpleasant, sometimes even scratchy.

The $D_{10}$, $D_{50}$ or $D_{90}$ value of the cumulative frequency distribution of the volume-averaged size distribution function, as is obtained by laser diffraction methods, indicates that 10%, 50% or 90%, respectively, of the micronized waxes or pigments have a diameter which is less than or equal to the value stated in each case. Here, the size distribution curve of the micronized waxes and pearlescent pigments is determined using an instrument from Malvern (instrument: Malvern Mastersizer 2000), the size distribution curve of the metal effect pigments (in powder form) using an instrument from Sympathec (instrument: Helos particle size analysis with Rodos dry dispersion and Vibri feeder) and the size distribution curve of the metal effect pigments (in paste form), and that of the organic and inorganic pigments using an instrument from Quantachrome (instrument: Cilas 1064), in each case in accordance with the manufacturer's instructions. The evaluation of the scattered-light signals was carried out by the Fraunhofer method or Mie theory, which also involves refractive behavior and absorption behavior of the pigments.

Micronized waxes are usually solid at room temperature (25° C.) and convert from the solid state to the liquid state above their melting range without decomposition. The consistency of the micronized waxes can range from solid to brittly hard. Micronized waxes can be translucent to opaque, and they can also be additionally colored with a cosmetically approved colorant. The micronized waxes can start to melt at a temperature as low as 40° C. Preferably, the melting range is between 51 and 399° C., further preferably between 71 and 389° C., particularly preferably between 91 and 379° C. and particularly preferably between 111 and 369° C. The melting range of the micronized waxes is determined here in accordance with the DGF (Deutsche Gesellschaft far Fettwissenschaften—German Society for Fat Science) standard method C-IV 3a using a melting point measuring device (model 5A 6797, Gallenkamp).

Micronized waxes which can be used are natural and/or synthetic waxes. Furthermore, micronized waxes which can be used are preferably natural and/or synthetic waxes colored using cosmetically approved colorants. Moreover, mixtures of in each case differently colored and/or uncolored micronized waxes can also be added to the nail varnish according to the invention or the pigment/wax mixture according to the invention.

Natural micronized waxes which can be used are, for example, micronized beeswax (INCI: Cera Alba Beeswax), micronized candelilla wax (INCI: Candellila Cera) or micronized carnauba wax (INCI: Copernicia Cerifera (Carnauba) Wax), commercially available e.g. as Carnauba Super-Micropowder (Kahl) or Microcare 350 (Micro Powders). It is of course also possible to add different natural micronized waxes to the nail varnish according to the invention or to the pigment/wax mixture according to the invention.

Mixtures of natural and synthetic micronized waxes can likewise be used. These include, inter alia, micronized carnauba/PE wax (INCI: Carnauba/Polyethylene), commercially available as e.g. Microcare 300, Microcare 310 (Micro Powders) or micronized carnauba/synthetic wax (INCI: Carnauba/Synthetic Wax), commercially available as e.g. Microcare 325 (Micro Powders).

Biodegradable biopolymers in micronized form such as e.g. polylactic acid (INCI: Polylactic Acid), commercially available e.g. as Ecosoft 608, Ecosoft 608X (Micro Powders) and Ecosoft 611 (INCI: Polylactic Acid Copernecia Cerifera (Carnauba) Wax, Micro Powders) can also be used in the nail varnish according to the invention or in the pigment/wax mixture according to the invention.

Micronized waxes which can be used are, inter alia, synthetic waxes (INCI: (Oxidized) Synthetic Wax), commercially available e.g. as Microease 110XF, Microease 1105, Microease 114 S, Microease 116 (Micro Powders), micronized PE waxes, commercially available e.g. as Ceraflour 990 or Ceraflour 991 (BYK-Chemie), as Ceridust VP 3610 or TP Ceridust 6050 M (Clariant), as PE Super Micropowder (INCI: Polyethylene, Kahl), as Micropoly 200, Micropoly 210, Micropoly 220, Micropoly 220L, Micropoly 2505 (INCI: (Oxidized) Polyethylene, Micro Powders) or as PE Microspheres (Cospheric), micronized PP waxes, commercially available as Ceraflour 913, Ceraflour 914, Ceraflour 915, Ceraflour 916 (BYK-Chemie) or as Mattewax 511 (INCI: Polypropylene, Micro Powders), micronized PMMA waxes (Polymethyl methacrylate, CAS: 9011-14-7), commercially available e.g. as PMMA Microspheres (Cospheric) or micronized polytetrafluoroethylene waxes (INCI: PTFE), commercially available as e.g. PTFE-Super Micropowder (Kahl), Microslip 519, Microslip 519 L (Micro Powders) or Ceridust 9202 F, Ceridust 9205 F (Clariant).

It is also possible to use mixtures of different micronized synthetic waxes such as, for example, of PE/polytetrafluoroethylene (INCI: Polyethylene/PTFE), commercially available e.g. as PE-PTFE Super Micropowder (Kahl), Microsilk 419 (Micro Powders) or Ceridust 3920 F or Ceridust 9325 F (Clariant), of PE/polytetrafluoroethylene/synthetic wax (INCI: Polyethylene/PTFE/Synthetic Wax), commercially available e.g. as Microsilk 418 (Micro Powders), of PP/polytetrafluoroethylene (INCI: Polypropylene/PTFE), commercially available inter alia as Microsilk 920 (Micro Powders) or of polyethylene/organic ester, such as Ceridust 3831 (Clariant).

A micronized bistearylethylenediamide wax, commercially available as Ceridust 3910 (Clariant), can likewise be used.

Synthetic micronized waxes colored with colorants can also be added to the nail varnish according to the invention or to the pigment/wax mixture according to the invention. Mention is to be made here inter alia of the colored microspheres, such as white, black, blue, green, orange, pink, purple, red, yellow or gray microspheres (Cospheric). Alternatively or additionally, substrates, e.g. hollow glass beads, coated with titanium dioxide, as known from US 2011/0052804 A1, can be used.

Depending on the nail varnish base, the micronized waxes can optionally also be added to the nail varnish according to the invention in the form of a dispersion. Examples of commercially available dispersions (Micro Powders) are Microspersion 220PC (INCI: Polyethylene, Isohexadecane), Microspersion 419PC (INCI: Polyethylene, PTFE, Isohexadecane), Microspersion 511PC (INCI: Polypropylene, Isodecane, Polyethylene) or Microspersion 519PC (INCI: PTFE, Isodecane, Polyethylene).

Preferably, uncolored synthetic micronized waxes are added to the nail varnish according to the invention. Preferably, uncolored synthetic micronized waxes are also used in the pigment/wax mixtures according to the invention.

In a further embodiment, mixtures which comprise at least one micronized wax and at least one type of hollow glass beads can also be added to the nail varnish according to the invention. Hollow glass beads which can be used are, for example, Hollow Glass Microspheres (sodium silicate CAS No. 1344-09-8, sodium borate CAS No. 7775-19-1, amorphous silicon dioxide CAS No. 7631-86-9; Cospheric). The average particle size $D_{50}$ of the hollow glass beads is in a range from 27 to 90 µm, preferably in a range from 45 to 75 µm and particularly preferably in a range from 53 to 63 µm. According to one preferred embodiment, the fraction of micronized wax, based on the total weight of micronized wax and hollow glass beads, is more than 50% by weight, furthermore preferably more than 65% by weight.

In a preferred embodiment, the nail varnish according to the invention comprises at least one pearlescent pigment and/or at least one metal effect pigment as well as the at least one micronized wax.

In a further embodiment, a mixture of colored and uncolored micronized waxes of identical or different particle size and/or of identical or different chemical composition of the wax matrix in the presence of at least one effect pigment can be added to the nail varnish according to the invention.

The nail varnish according to the invention can be produced by combining at least one micronized wax, at least one effect pigment and a nail varnish base.

The order in which the components of the nail varnish according to the invention that are responsible for the haptic and/or the optical effect are added is not decisive. The at least one micronized wax is preferably added in solid form to the nail varnish according to the invention. Preferably, the components of the nail varnish according to the invention that are not soluble in the nail varnish base, i.e. micronized wax(es) and pigment(s), are added in succession or as a mixture of a nail varnish base which is uncolored or colored with a soluble dye. It is therefore possible to produce the nail varnish according to the invention very easily. In order to largely avoid damage to platelet-like effect pigments as a result of any shear forces acting, it is preferred to add these towards the end of the combining or mixing of the components.

According to the invention, nail varnish base is intended to mean the composition which comprises the components required for a nail varnish such as film formers, resins, plasticizers, solvents and thixotropic agents, but not micronized wax(es). Optionally, further components, e.g. preservatives, UV absorbers or fragrances can additionally be added to the nail varnish base.

The nail varnish base may be a commercially available nail varnish base such as, for example, International Lacquers Nailpolish & Care Base 359 (International Lacquers) or the Intermediates (Durlin). Furthermore, it is also possible to use a UV-curing nail varnish base. Alternatively, the nail varnish base can be formulated directly using the customary raw materials by the methods known to the person skilled in the art. Film formers which can be used are, for example, nitrocellulose, ethylcellulose or cellulose acetate, and resins which can be used are e.g. polyester resins or polyvinyl acetate. Plasticizers which can be mentioned are, for example, dibutyl phthalate, tricresyl phosphate, triethyl citrate or camphor. The customary solvents used are e.g. ethyl acetate, isopropanol or n-butyl acetate. The thixotropic agents include, inter alia, stearylalkonium bentonite or hectorite. The nail varnish base can optionally already be colored or pigmented by adding soluble or insoluble colorants.

Furthermore, an aqueous nail varnish system can also be used as nail varnish base. However, in this case, it is to be ensured that the pigments used, in particular the metal effect pigments, are suitable for use in water-based systems.

The at least one effect pigment and also the at least one micronized wax is compatible with a large number of commercially available colored or uncolored nail varnish base systems. By virtue of the countless combination possibilities of at least one effect pigment and at least one micronized wax, different optical and haptic effects can be achieved in a very simple way depending on the effect pigment used and the micronized wax used.

In order to achieve this unique combination of optical and haptic effect, surprisingly, no repeated painting of a fingernail is necessary. Since as a rule the micronized wax causing predominantly the haptic effect is added to the nail varnish directly in solid form, no complicated multilayer varnish layer build-up on a fingernail with, for example, one layer responsible for the haptic effect and one layer responsible for the optical effect is necessary. The nail varnish according to the invention surprisingly has, after application and drying, excellent mechanical stability and is not damaged by customary housework and/or office work, but is retained over a period of at least two days on the painted fingernail in an optically attractive way. Furthermore, the nail varnish according to the invention exhibits, after application and drying, sufficient chemical stability toward skin care products, such as, for example, a hand cream and/or customary domestic cleaners, e.g. dishwashing detergents.

The countless combination possibilities of different colorants with different colored or uncolored micronized waxes in each case in a different particle size permit a multitude of optical and haptic effects in a simple way. An effect pigment in different particle sizes, such as e.g. a metal effect pigment, can be combined with a micronized wax in different particle sizes such that the metal effect pigment with a small particle size with e.g. an average particle size $D_{50}$ from a range from 5 to 27 µm is present in each case with micronized waxes of a low particle size ($D_{50}$ from a range from 2.5 to 20 µm), an average particle size ($D_{50}$ from a range from >20 to 30 µm) and/or a coarse particle size ($D_{50}$ from a range from >30 to 91 µm) in the nail varnish according to the invention. The same of course applies also for metal effect pigments with average particle sizes ($D_{50}$ from a range from >27 to 45 µm) or coarse particle sizes ($D_{50}$ from a range from >45 to 71 µm). Besides a variation in the micronized waxes, the metal effect pigment can be used in different particle sizes also with at least one further metal effect pigment, at least one pearlescent pigment, at least one organic and/or inorganic colored pigment of identical or different particle size or in the presence of at least one colorant present in dissolved form in the respective nail varnish system. Thus, for example, it is also possible for a mixture of an aluminum effect pigment and of a gold bronze effect pigment in the presence of a micronized wax to be present. In the nail varnish according to the invention, it is not only possible for the colorants to be varied and/or combined with one another in different ways depending on the desired color and the optical effect to be achieved, but the micronized waxes used can also be used in very different particle sizes, meaning that, as a result of the interplay of the two components, a unique combination of optical and haptic effects can be realized. A nail varnish according to the invention here can also comprise a mixture of micronized waxes of identical or different particle size. The combination possibilities for metal effect pigments, listed above by way of example and nonexhaustively, also apply accordingly for pearlescent pigments to be used, organic or inorganic pigments. The nail varnish base here can be uncolored or colored with at least one soluble dye.

A particular feature when using magnetic effect pigments, such as, for example, platelet-like iron pigments, is that these are still magnetically orientable in the nail varnish according to the invention despite the presence of the at least one micronized wax. The magnetic effect pigments can be arranged on a freshly painted fingernail by applying an external magnetic field to generate visible patterns, and the patterns produced depending on the magnet used are fixed by drying. Sometimes, in addition to the optical and haptic effects already described, a painted fingernail has patterns induced by the applied magnetic field. The magnetic effect pigments can of course also be present in a mixture with further colorants in the nail varnish according to the invention.

If a nail varnish base, which can optionally be colored with a dye, is modified by adding at least one micronized wax, then the haptic effect change perceptible on the painted fingernail compared to the nail varnish base without the addition of micronized wax is exclusively attributable to the at least one micronized wax. With increasing particle size of the at least one micronized wax, a fingernail painted in this way is given an increasingly velvet-like effect, which can also be referred to as "soft touch" effect.

In the presence of an organic or inorganic colored pigment, the micronized wax, following application and drying of the nail varnish according to the invention, generally influences predominantly the haptic impression. Both in the case of the colorants soluble in the nail varnish and also in the case of organic or inorganic absorption pigments, a viewer perceives essentially the same color impression over the entire fingernail irrespective of angle. As a result of adding at least one micronized wax, a nail varnish colored and/or pigmented in this way loses its original shine and is more matt. This effect can be pronounced to different extents depending on the particle size of the at least one micronized wax. The larger the particle size of the at least one micronized wax, the more matt a nail varnish provided with at least one absorption pigment. The amount of the at least one micronized wax added also has an influence on the haptic and optical properties of the nail varnish according to the invention. The higher the fraction in % by weight of the at least one micronized wax in the nail varnish formulation, the more matt the applied and dried nail varnish appears to a viewer.

In contrast to absorption pigments, platelet-like effect pigments exhibit an angle-dependent appearance. The optical effect of the platelet-like effect pigments is based on the directed reflection of light at predominantly flat pigment particles arranged essentially parallel relative to one another. Depending on the substrate and coating(s) applied thereto, interference, reflection and/or absorption phenomena produce different color and/or brightness impressions. By virtue of its slight curvature and its smoother surface compared to human skin, a human fingernail constitutes a good substrate for an application of nail varnishes pigmented with effect pigments. Sometimes, the angle-dependent optical impression typical of the particular effect pigment is also clearly evident on a fingernail which has been painted with an effect-pigmented nail varnish. In contrast to nail varnishes admixed with absorption pigments, nail varnishes pigmented with effect pigments exhibit a different appearance depending on the angle. A fingernail which has been painted with a nail varnish comprising metal effect pigments exhibits the typical metal shine at the specular angle (90° relative to the angle of incidence of the light irradiated at 45°). Outside of the specular angle, nail varnishes of this type are less shiny and darker. This phenomenon is referred to as light/dark flop. If a fingernail is provided with a nail varnish comprising pearlescent pigments, then said varnish gives the fingernail, at the specular angle, the deep shine typical of pearlescent pigments with simultaneous transparency. This effect too becomes increasingly lost outside of the specular angle.

In the presence of at least one micronized wax, nail varnishes which comprise effect pigments exhibit, compared to the corresponding nail varnish application without micronized wax, an effect and/or shine loss at the specular angle in the application. However, applications of this type surprisingly exhibit a more uniform optical effect for a viewer over the entire angle range, these being shine, brightness and/or interference effects depending on the at least one effect pigment used. The angle dependency of the optical impression characteristic of effect pigments is thus attenuated in a targeted manner. As well as this optical effect, the presence of at least one micronized wax also makes itself noticeable from a haptic point of view. When using effect pigments, the haptic effect is attributed not exclusively to the micronized wax, but the at least one effect pigment also plays a certain role here depending on particle size and/or pigmentation level. An effect pigment of very fine particle size, i.e. with an average particle size $D_{50}$ from a range from 1 to 15 µm, plays a minor role with regard to the haptic effect compared to nail varnish applications comprising a micronized wax with increasing particle size. The optical effect of a comparison of this type changes from a very homogeneous and silky appearance to a more lively appearance. Effect pigments gain more influence on the optical and haptic effect with increasing particle size. Moreover, effect pigments with a relatively large particle size, for example an average particle size $D_{50}$ from a range from >15 to 100 µm, are responsible for glittery nail varnish applications. This glitter effect is all the more pronounced the greater the micronized wax present in the nail varnish.

As well as the optical and haptic effects explicitly described here, it is already evident from the large number of combination possibilities of at least one colorant and at least one micronized wax that significantly more different effects can also be achieved. Sometimes, a large number of optical and haptic effects is accessible in a surprisingly simple manner. The combination desired in each case of optical and/or haptic properties of the nail varnish according to the invention can be adjusted through appropriate choice of at least one colorant and at least one micronized wax.

The individual assessment of the haptic velvet-like effect described is determined by tactile perception. The velvet-like effect can be referred to inter alia as "soft touch" or "soft feel" effect.

The optical effect of the nail varnish according to the invention in the presence of at least one micronized wax can be described, following application and drying, for example by the terms "non-shiny", "satin finish" or "frosted matt".

In principle, by increasing the weight fraction of micronized wax, the nail varnish according to the invention, after application and drying, can be given a more pronounced velvet-like effect. The upper limit of the addition of micronized wax can be co-determined by the properties of the particular nail varnish base and can be ascertained experimentally by corresponding concentration series. If too large an amount of micronized wax is added, the viscosity can be considerably increased and thus the applicability on the nail impaired. According to the invention, an addition amount of micronized wax in the range from 0.1 to 25% by weight, preferably in the range from 1.0 to 20% by weight, in each case based on the total weight of the nail varnish according to the invention, has proven useful. In the case of a combination with effect pigments, the amount of the at least one micronized wax is preferably in a range from 1 to 15% by weight, particularly preferably in a range from 3 to 10% by weight, in each case based on the total weight of the nail varnish according to the invention.

Organic and inorganic pigments can be added to the nail varnish according to the invention in a range from 0.05 to 2.5% by weight, preferably in a range from 0.06 to 1.0% by weight and particularly preferably in a range from 0.07 to 0.5% by weight, in each case based on the total weight of the nail varnish according to the invention. Organic and inorganic pigments are preferably added to the nail varnish according to the invention in the form of dispersions.

Effect pigments are used in the nail varnish according to the invention preferably in a range from 0.05 to 6.0% by weight, particularly preferably in a range from 0.1 to 5.0% by weight, further preferably in a range from 0.15 to 4.0% by weight and very particularly preferably in a range from 0.2 to 3.5% by weight, in each case based on the total weight of the nail varnish according to the invention.

The nail varnish according to the invention can comprise a mixture with at least one effect pigment and at least one micronized wax in the ratio of 10 to 49% by weight of effect pigment to 51 to 90% by weight of micronized wax, in each case based on the total weight of the components effect pigment and micronized wax.

In a preferred embodiment, the ratio of the average particle size $D_{50}$ of the at least one effect pigment that can be used in the nail varnish according to the invention to the average particle size $D_{50}$ of the at least one micronized wax according to formula (I)

$$\frac{D_{50} \text{ effect pigment}}{D_{50} \text{ micronized wax}} \qquad (I)$$

is in a range from 0.1 to 12.0, preferably in a range from 0.2 to 10.3, particularly preferably in a range from 0.3 to 7.2 and very particularly preferably in a range from 0.4 to 4.9.

In a further preferred embodiment, the ratio of the average particle size $D_{50}$ of the at least one pigment which can be used in the mixture according to the invention to the average particle size $D_{50}$ of the at least one micronized wax according to formula (II)

$$\frac{D_{50} \text{ pigment}}{D_{50} \text{ micronized wax}} \quad \text{(II)}$$

is in a range from 0.1 to 12.0, preferably in a range from 0.2 to 10.3, particularly preferably in a range from 0.3 to 7.2 and very particularly preferably in a range from 0.4 to 4.9.

It has surprisingly been found that upon establishing the aforementioned ratio after application and drying of the nail varnish according to the invention, extraordinary optical effects, in particular silky shine or glitter effects, etc., are retained for a viewer. Moreover, the nail varnish according to the invention is characterized, after application and drying, by pleasant velvet-like sensory properties.

In contrast to nail varnishes without micronized wax(es), nail varnishes which comprise micronized wax(es) are characterized by an optical depth effect of the applied and dried nail varnish film. A nail varnish which comprises for example exclusively a metal effect pigment and no micronized wax, as already described, exhibits, following application and drying, an essentially angle-dependent shine effect and/or a so-called light/dark flop. This change in brightness is described by the flop index. The flop index is defined in accordance with Alman as follows (S. Schellenberger, M. Entenmann, A. Hennemann, P. Thometzek, Farbe and Lack, 04/2007, p. 130):

$$\text{Flop index} = 2.69 \cdot (L_{E1} - L_{E3})^{1.11} / L_{E2}^{0.86}$$

where $L_{E1}$ is the brightness of the near-specular measuring angle (E1=15° relative to the specular angle), $L_{E2}$ is the brightness of the measuring angle between near-specular and far-specular angle (E2=45° relative to the specular angle) and $L_{E3}$ is the brightness of the far-specular measuring angle (E3=110° relative to the specular angle). The larger the numerical value of the flop index, the more greatly the light/dark flop is expressed.

For a viewer, the optical impression of the nail varnish application here is dependent on the particle size and also on the type of metal effect pigment. For example, thin fine metal effect pigments with an average particle size $D_{50}$ from a range from 5 to 27 μm and an aspect ratio, i.e. a ratio of pigment diameter to pigment thickness, in the range from 50 to 200 make a painted fingernail at the specular angle shine like liquid metal. This effect is even greater in the case of very thin metal effect pigments produced by PVD methods. Outside of the specular angle, however, this nail varnish application appears somewhat dark and non-shiny to a viewer. If at least one micronized wax is added to a nail varnish provided with the PVD metal effect pigment, then a viewer now surprisingly perceives, following application and drying, a certain glitter effect over the entire viewing angle. At the specular angle, the greater metallic shine and the marked light/dark flop of a nail varnish application without micronized wax cannot then be perceived or can only be perceived in a considerably attenuated form. As a result of adding micronized wax, the nail varnish application according to the invention is overall more lively.

In order to be able to objectively describe the optical influence of the at least one micronized wax in the presence of at least one effect pigment, multi-angle color measurements and effect measurements were carried out using a BYK-mac (BYK-Gardner) by reference to nail varnish applications on black-white coverage cards (chart PA-2812, BYK-Gardner). The BYK-mac measures the total color impression under different viewing angles and light ratios. The multi-angle color measurement serves here to ascertain and describe the light/dark flop and/or color flop of nail varnishes provided with effect pigments. The measurement geometries (−15°), +15°, 25°, 45°, 75°, 110° are measured relative to the angle of emergence of the light irradiated at 45°. To simulate effect changes upon direct and diffuse illumination, glitter effect and graininess are simultaneously monitored with the help of a high-resolution CCD camera. The glitter effect, caused by the reflecting ability of the individual effect pigments, is only perceived upon direct solar irradiation and changes depending on the illumination angle. For this reason, the BYK-mac illuminates the sample with very bright LEDs at three different angles (15°/45°/75°, FIG. 1). The CCD camera takes an image in each case perpendicularly to the surface. The images are analyzed using image processing algorithms, using the histogram of the brightness stages as a basis for calculating the glitter parameters. In order to ensure better differentiation, the glitter effect can be described by a two-dimensional system, the glitter area S_a and the glitter intensity S_i, which can also be summarized in a one-dimensional value, the glitter degree S_G (BYK-Gardner, catalog "Qualitätskontrolle für Lacke and Kunststoffe [Quality control for coatings and plastics]" 2011/2012, pp. 97/98).

The measured glitter area and glitter intensity is influenced by the orientation of the effect pigments. An effect pigment with good arrangement, i.e. largely plane-parallel to the substrate, has, in a comparison of the glitter measurement values S_a, S_i and S_G obtained in the illumination geometries 15°, 45° and 75°, the highest measurement values at an illumination geometry of 15° since a large part of the effect pigments directly reflects the incident light. At an illumination geometry of 45°, the incident light is largely reflected directly and thus perceived as a weaker glitter effect when observed perpendicularly to the application. The glitter effect observed at this illumination geometry is attributed partly to incorrectly, i.e. non-plane-parallel, oriented effect pigments which are able to deviate the light irradiated at 45° in the direction of the detector. At an illumination geometry of 75°, no or only a weak glitter effect is perceived perpendicularly to the application. This effect is in turn caused by incorrectly arranged effect pigments.

Consequently, a well-oriented effect pigment has the greatest glitter effect at 15°; the minimum glitter effect is observed at 75°. In the case of a poorly oriented effect pigment, the differences of the measurement values observed at 15°, 45° and 75° illumination geometry are smaller since light is always reflected in the direction of the detector as a result of the incorrect orientation.

Figure 2:
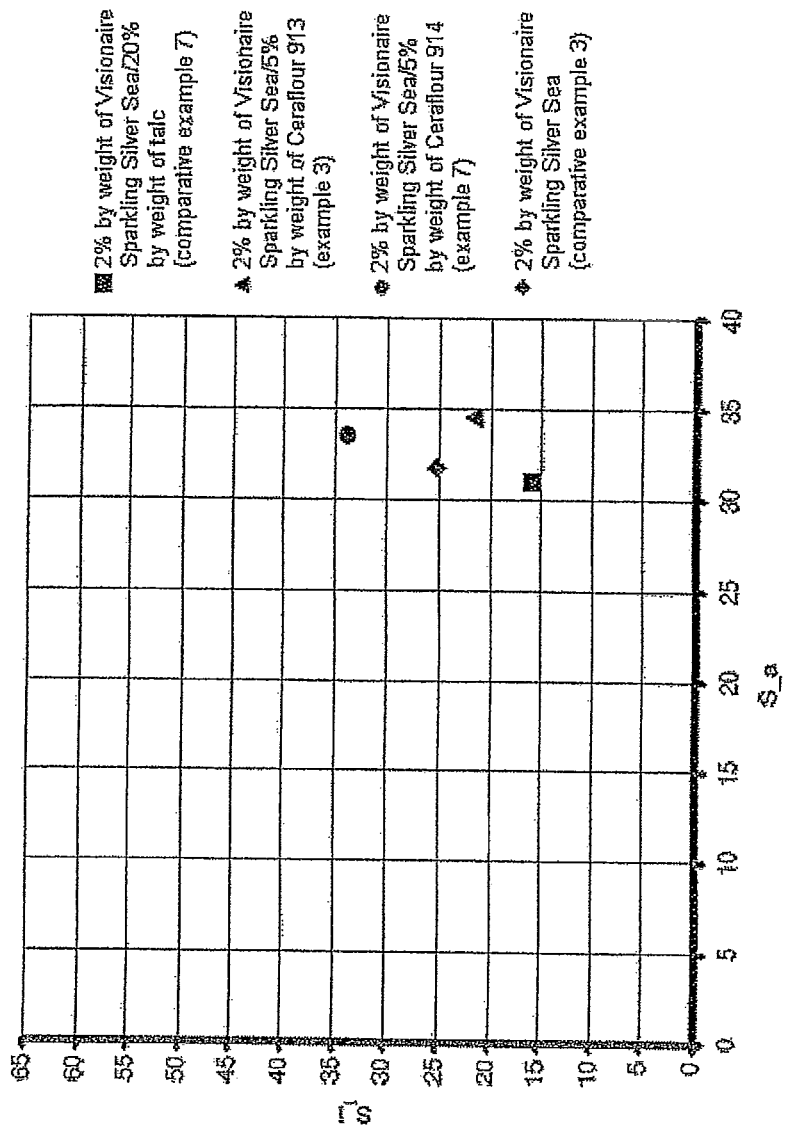
FIG. 2 is a graph of the glitter area S_a and glitter intensity S_i of a nail varnish application comprising the metal effect pigment Visionaire Sparkling Silver Sea without the addition of micronized wax (comparative example 3), in the presence of Ceraflour 913 (example 3), Ceraflour 914 (example 7) and talc (comparative example 7) at a measurement geometry of 15° (measured on black substrate of a black-white coverage card)
Figure 3:
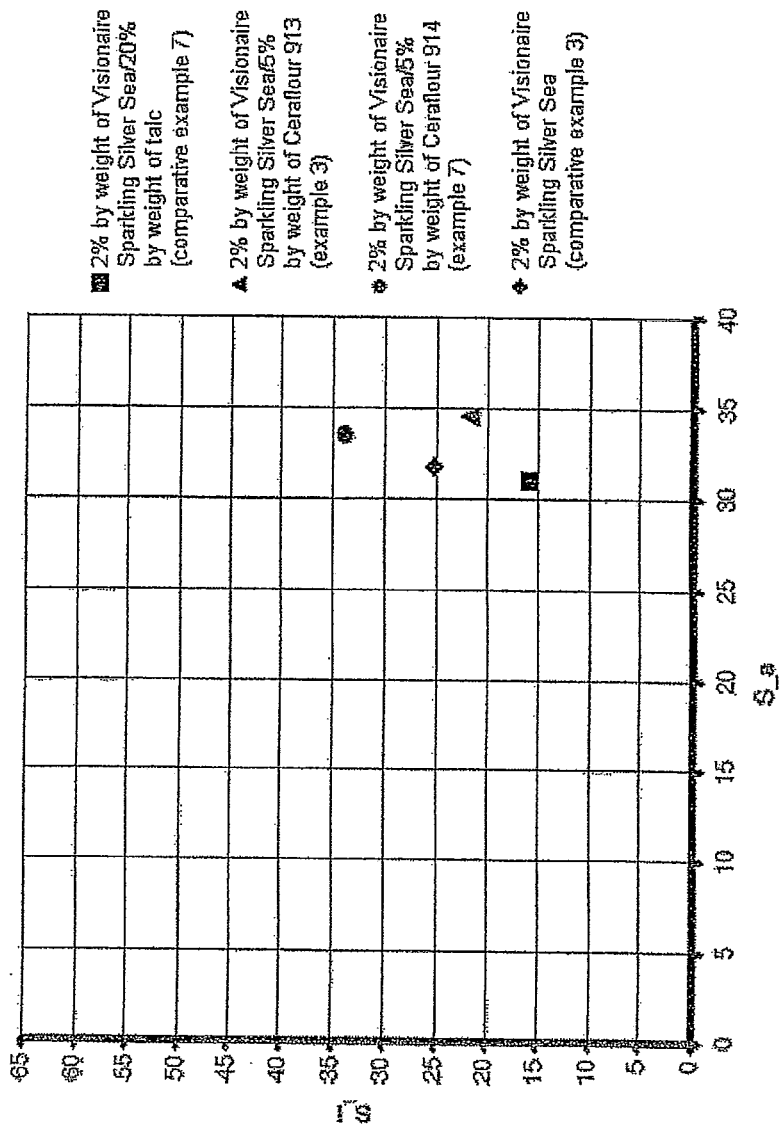
FIG. 3 is a graph of the glitter area S_a and glitter intensity S_i of a nail varnish application comprising the metal effect pigment Visionaire Sparkling Silver Sea without the addition of micronized wax (comparative example 3), in the presence of Ceraflour 913 (example 3), Ceraflour 914 (example 7) and talc (comparative example 7) at a measurement geometry of 45° (measured on black substrate of a black-white coverage card)
Figure 4:
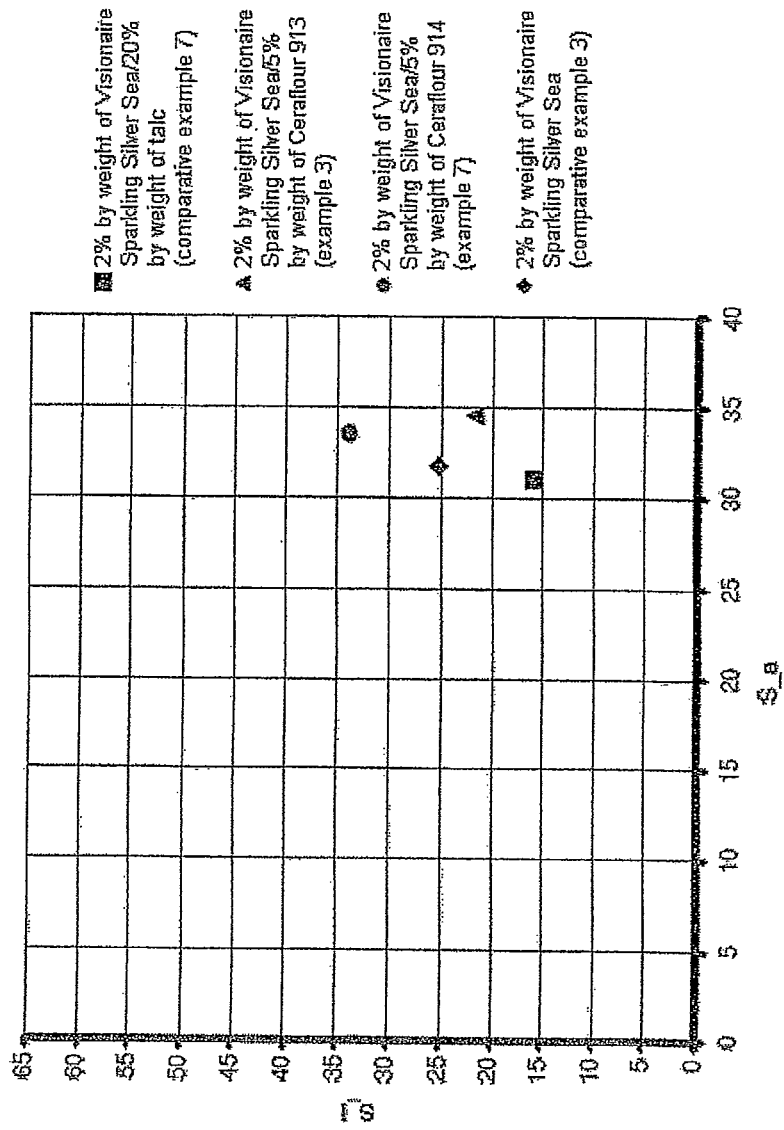
FIG. 4 is a graph of the glitter area S_a and glitter intensity S_i of a nail varnish application comprising the metal effect pigment Visionaire Sparkling Silver Sea without the addition of micronized wax (comparative example 3), in the presence of Ceraflour 913 (example 3), Ceraflour 914 (example 7) and talc (comparative example 7) at a measurement geometry of 75° (measured on black substrate of a black-white coverage card)

Hereinbelow, by way of example, the glitter values measured using the BYK-mac are explained by reference to the example of a coarse metal effect pigment with an average particle size of 45 to 71 μm (Visionaire Sparkling Silver Sea, Eckart) (FIGS. 2 to 4). If the application of a nail varnish comprising a coarse metal effect pigment without the addition of at least one micronized wax is measured on a black-white coverage card (chart PA-2812, BYK-Gardner), then an increasing reduction in the glitter degree S_G is observed starting from the 15° illumination geometry. However, if the effect pigment orientation is disturbed by adding at least one micronized wax, then the measurement values of the glitter degree S_G observed at 15°, 45° and 75° illumination geometry get closer together. It is assumed that by adding at least one micronized wax, an incorrect orientation of the coarse metal effect pigment is induced such that a clearly perceptible number of metal effect pigments reflects the incident light onto the detector.

If, instead of the at least one micronized wax for achieving a matt nail varnish, a standard commercial matting agent such as, for example, talc were used, then a considerably larger amount of matting agent would have to be added to achieve a comparable optical effect. In the case of talc, at least 15% by weight, based on the total weight of the nail varnish, would have to be used in order to achieve a comparable matting effect in the example given above. However, the high proportion of opaque talc particles then results in the loss of the glitter intensity S_i.

The one-dimensional glitter degree S_G is decisive for the optical impression. The higher the numerical value of S_G, the higher the glitter effect that can be perceived even by the eye. In a two-dimensional representation, the glitter degree S_G can be divided into the components glitter intensity S_i and glitter area S_a. Since both components have a decisive influence on the glitter degree S_G, what can happen is that an effect pigment has virtually the same glitter degree S_G in the measurement geometries 15°, 45° and 75° although the numerical values of S_a and S_i increase or decrease significantly in the viewed angles.

Figure 5:
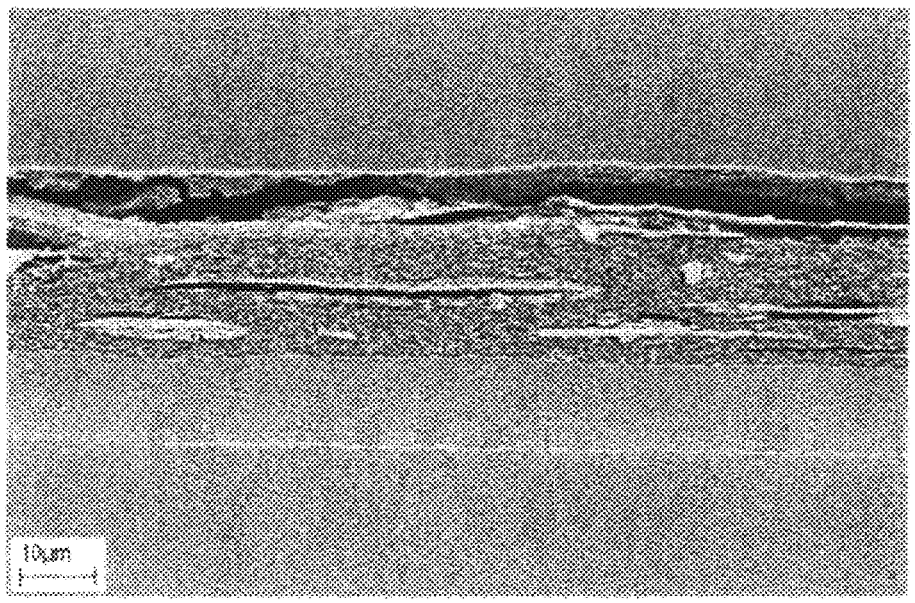
FIG. 5 is a scanning electron micrograph in transverse section of a nail varnish application comprising the metal effect pigment Visionaire Sparkling Silver Sea without the addition of micronized wax (comparative example 3)
Figure 6:
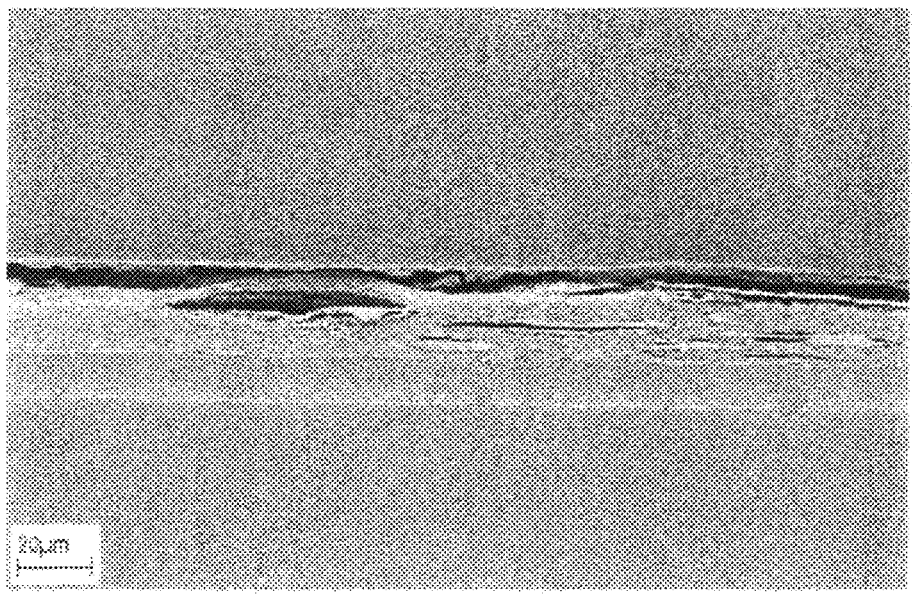
FIG. 6 is a scanning electron micrograph in transverse section of a nail varnish application comprising the metal effect pigment Visionaire Sparkling Silver Sea without the addition of micronized wax (comparative example 3)
Figure 7:
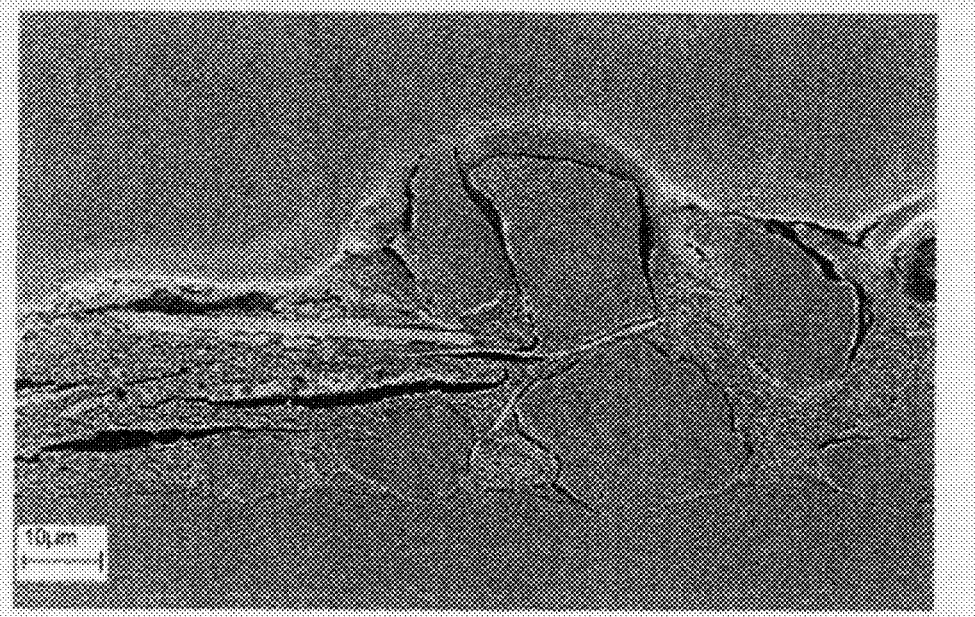
FIG. 7 is a scanning electron micrograph in transverse section of a nail varnish application comprising the metal effect pigment Visionaire Sparkling Silver Sea and the micronized wax Ceraflour 914 (example 7)
Figure 8:
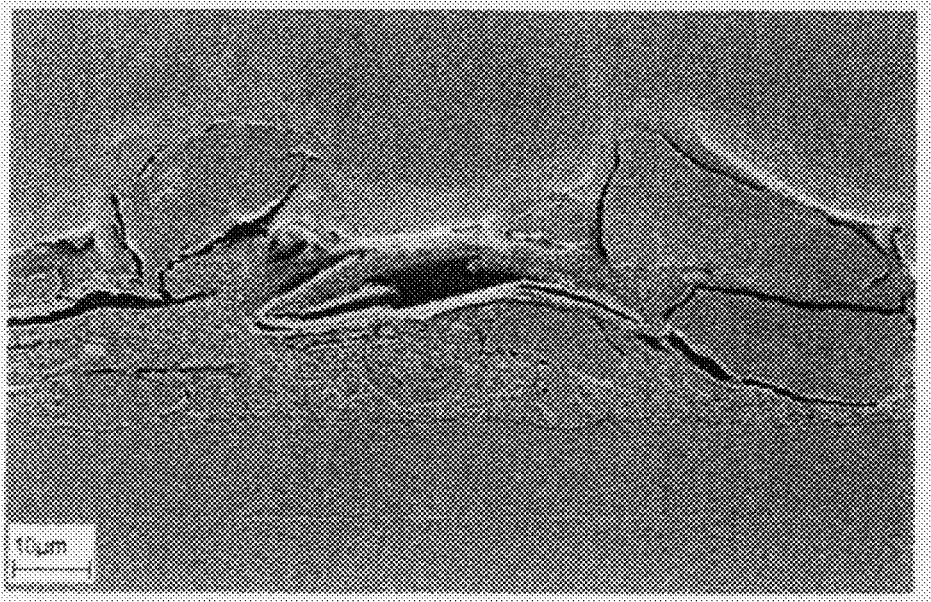
FIG. 8 is a scanning electron micrograph in transverse section of a nail varnish application comprising the metal effect pigment Visionaire Sparkling Silver Sea and the micronized wax Ceraflour 914 (example 7)
Figure 9:
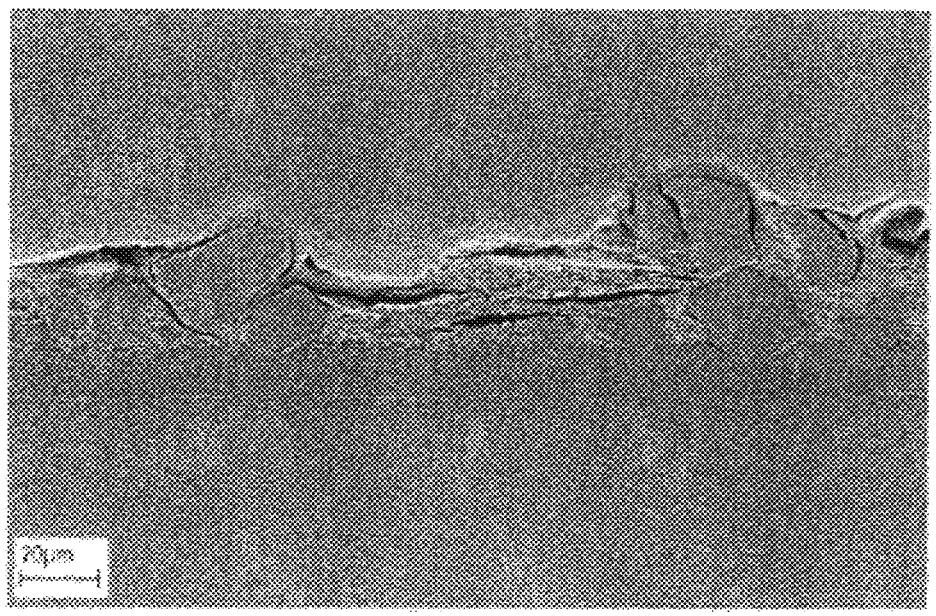
FIG. 9 is a scanning electron micrograph in transverse section of a nail varnish application comprising the metal effect pigment Visionaire Sparkling Silver Sea and the micronized wax Ceraflour 914 (example 7)
Figure 10:
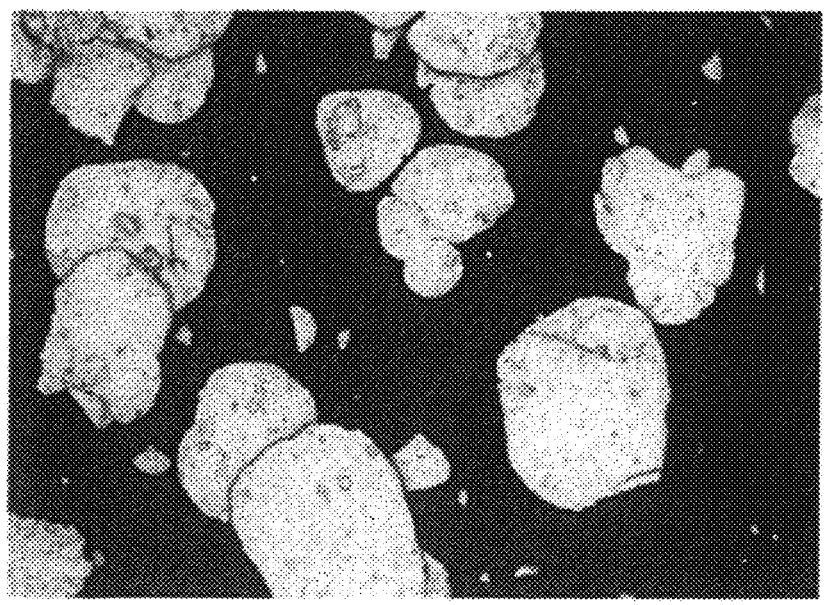
FIG. 10 is a light micrograph (500 times magnification) of a nail varnish application comprising the metal effect pigment Visionaire Sparkling Silver Sea (comparative example 3)
Figure 11:
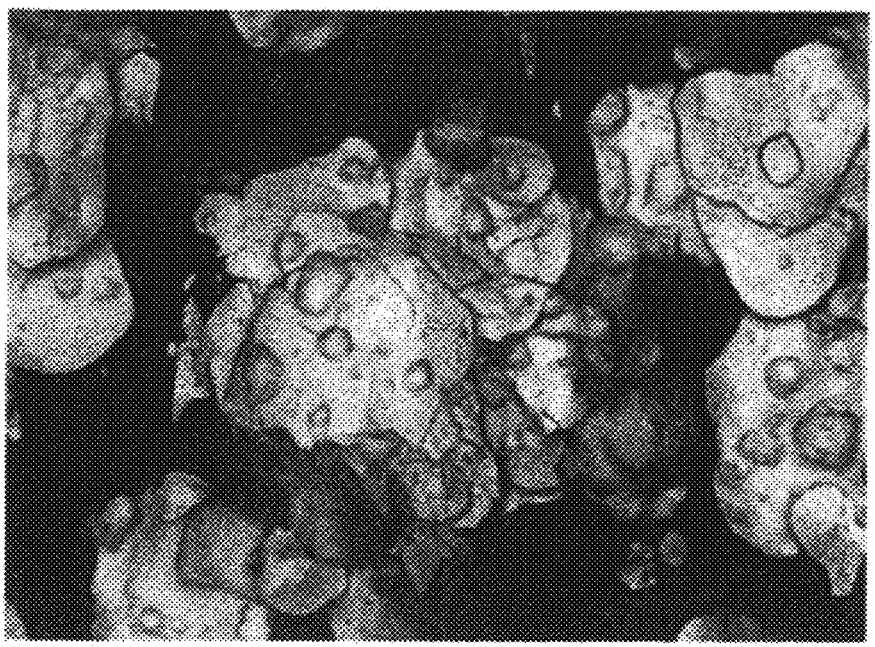
FIG. 11 is a light micrograph (500 times magnification) of a nail varnish application comprising the metal effect pigment Visionaire Sparkling Silver Sea and the micronized wax Ceraflour 913 (example 3)
Figure 12:
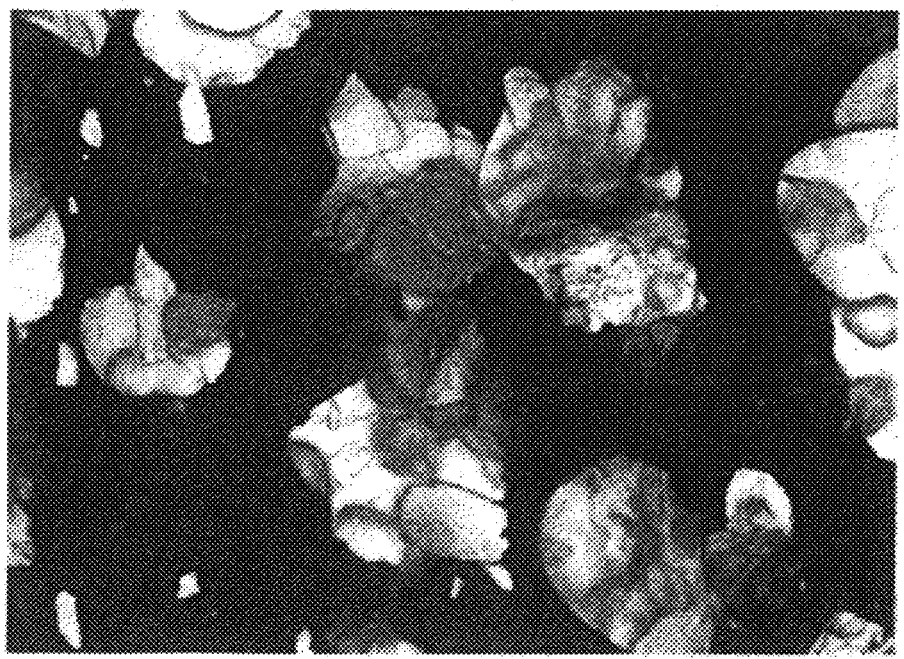
FIG. 12 is a light micrograph (500 times magnification) of a nail varnish application comprising the metal effect pigment Visionaire Sparkling Silver Sea and the micronized wax Ceraflour 914 (example 7)
Figure 13:
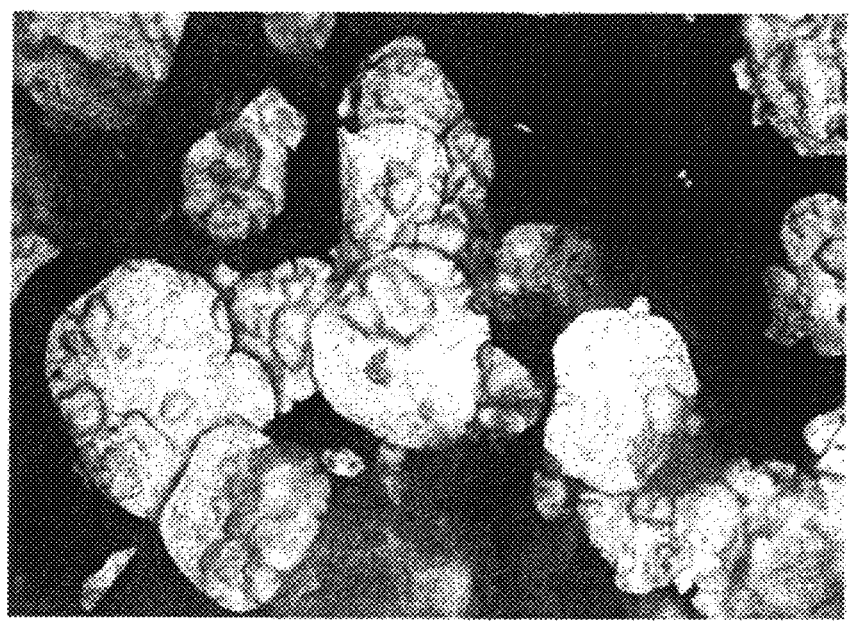
FIG. 13 is a light micrograph (500 times magnification) of a nail varnish application comprising the metal effect pigment Visionaire Sparkling Silver Sea and talc (comparative example 7)

Nail varnishes without the addition of micronized wax permit a largely plane-parallel arrangement of platelet-like effect pigments relative to the respective substrate. FIG. 5 and FIG. 6 show a scanning electron micrograph of a nail varnish in transverse section comprising a metal effect pigment. Here, the optimum plane-parallel orientation of the metal effect pigment can be seen very clearly. In the presence of at least one micronized wax, a plane-parallel arrangement of a platelet-like effect pigment relative to the particular substrate is not always possible, meaning that the platelet-like effect pigments are forced, depending on their own particle size and the particle size of the at least one micronized wax, into a greater or lesser pronounced incorrect arrangement, i.e. an arrangement that is no longer parallel relative to the substrate. In FIGS. 7 to 9, an incorrect positioning of this type of a metal effect pigment, caused by the presence of a micronized wax, is shown in transverse section by reference to a scanning electron micrograph. As a result of this non-optimum arrangement of the platelet-like effect pigments, a considerable degree of shine is lost at the specular angle. Instead, as a result of this incorrect arrangement of the platelet-like effect pigments, from different viewing angles, platelet-like effect pigments are always turned to face a viewer at the specular angle, which makes them noticeable due to their shine and/or glitter effect. Thus, as a result of the presence of micronized wax, a viewer perceives a reduced effect at the specular angle, instead a notable glitter effect over a larger angle range. Moreover, the addition of at least one micronized wax even in a comparatively small use amount, for example <10% by weight, based on the total weight of the nail varnish according to the invention, brings about the desired velvet-like, visually more matt effect. For a use amount of <10% by weight of talc, although an attenuation of the metallic shine is achieved, the applied nail varnish has, as before, an angle-dependent metallic shine effect.

Figure 14:
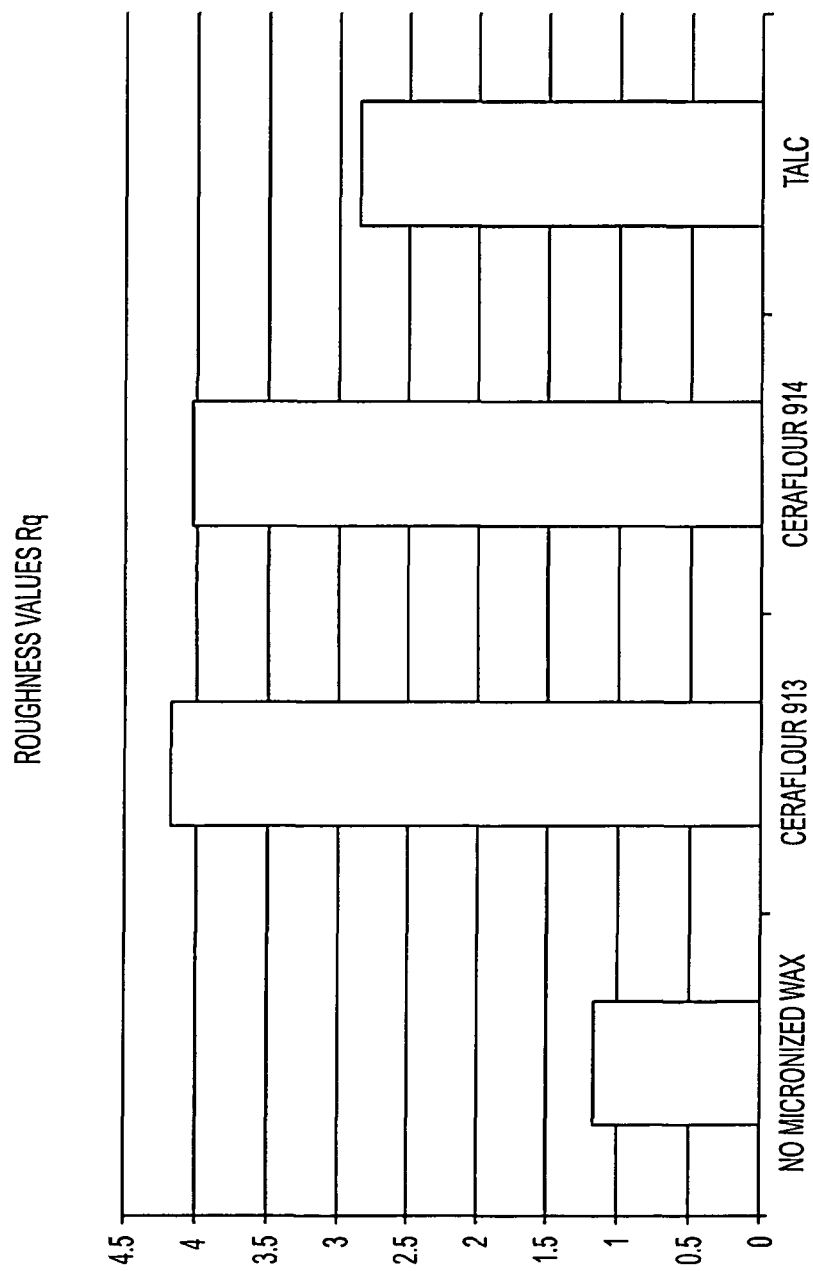
FIG. 14 is a bar chart of roughness values Rq of nail varnish applications comprising the metal effect pigment Visionaire Sparkling Silver Sea without the addition of micronized wax (comparative example 3), in the presence of Ceraflour 913 (example 3), Ceraflour 914 (example 7) and talc (comparative example 7).

The haptic effect can also be ascertained using light-microscopic depth profiles of the nail varnishes according to the invention. The nail varnish applications were created for this purpose on black-white coverage cards (chart PA-2812, BYK-Gardner) and, after drying, measured using the microscope Axio Imager.Zlm (Zeiss). Above a height range of ca. 30 μm perpendicular to the black-white coverage card, two microscope images were recorded in each case per micrometer, and these were then superimposed using the image processing software AxioVision 4.6.3. to give a single microscope image (FIGS. 10 to 13) and at the same time were recalculated to give a topography image. This topography image was used to calculate the surface parameter "roughness value" Rq in accordance with DIN EN ISO 4287:2010-07 (FIG. 14). The comparison used was an identically pigmented nail varnish without the addition of micronized wax. Effect pigments orientate themselves in a nail varnish in the absence of micronized wax largely parallel to the substrate of the black-white coverage card which, as already described, is reflected optically in the high shine, glitter and/or brightness values and haptically in a very smooth surface with correspondingly low roughness values. Here, it should be taken into consideration that the surface quality is additionally influenced by the morphology of the nail varnish layer arranged over the effect pigments, i.e. the assessment of the haptics has to be made in principle in relation to the nail varnish system used in each case. An unpigmented nail varnish base not provided with micronized wax which, in application, has more rough, possibly even sand-paper-like haptics can be changed in a targeted manner by adding at least one micronized wax, such that feelably modified haptics result. In the same way, a nail varnish base that is smooth in application is modified in feel by adding at least one micronized wax. Consequently, the nail varnish base used in the course of such a comparison must of course be identical. Ideally, to optimize the optical and haptic effect, only one parameter at a time is changed, i.e. either the fraction of micronized wax is varied while keeping the pigment content constant, or the pigment fraction is varied while keeping the wax content constant. If micronized waxes are now added to a nail varnish provided with effect pigments, the effect pigments are disturbed in their optimum orientation. The presence of the micronized wax then leads to a change both with regard to the optical properties and also with regard to the haptic properties. Compared to a nail varnish without micronized wax, a significant increase in the roughness value is observed. If, instead of the at least one micronized wax, talc was now used, then a significantly higher amount of talc would have to be added to the nail varnish to achieve a comparable roughness value. Thus, for example, even by adding 20% by weight of talc, following application and drying of the nail varnish, the roughness value of a corresponding nail varnish according to the invention but provided with 5% by weight of micronized wax is not achieved (FIG. 14).

In a further embodiment of the invention, at least one pigment and at least one micronized wax can be present in a mixture. This mixture can be added to a colored or uncolored nail varnish base.

Preferred mixing ratios in % by weight, in each case based on the total weight of the components pigment, preferably effect pigment, particularly preferably pearlescent pigment and/or metal effect pigment, and micronized wax are 10 to 49 (pigment) to 51 to 90 (micronized wax), particularly preferred mixing ratios are 18 to 34 (pigment) to 66 to 82 (micronized wax), very particularly preferred mixing ratios are 22 to 33 (pigment) to 67 to 78 (micronized wax).

Suitable mixtures of at least one pigment and at least one micronized wax can be produced depending on the desired optical and haptic effect in the nail varnish following application and drying. It is of course also possible to use different pigments or identical pigments of different particle size in such a mixture. The micronized waxes can also be varied accordingly. Preferably, the pigments used are pearlescent pigments and/or metal effect pigments. An additional coloring can take place by at least one dye.

In a further embodiment, these mixtures are pigment/wax mixtures without the additional addition of a solvent or are so-called dedusted pigment/wax mixtures which can be obtained, for example, by adding a small amount of solvent and/or water of less than 10% by weight, based on the total weight of the pigment/wax mixture. To produce solvent-containing pigment/wax mixtures, preference is given to using solvents or solvent mixtures in which the at least one micronized wax component does not dissolve.

In a further embodiment, further typical nail varnish components such as, for example, preservatives, fillers and/or rheology-modifying additives, can be added to the pigment/wax mixtures.

In the case of pasty water-containing and/or solvent-containing pigment preparations, the addition of the at least one micronized wax can take place for example in the dispersion by admixing before the homogenized dispersion is concentrated by customary methods such as filtration by means of filter press and converted to a pasty application form.

In a further embodiment, the pigment/wax mixture comprises at least one effect pigment, preferably at least one metal effect pigment and/or at least one pearlescent pigment, and at least one micronized wax with an average particle size $D_{50}$ from a range from 2.5 to 91 μm.

In a further embodiment, the pigment/wax mixture comprises at least one effect pigment, preferably at least one metal effect pigment and/or at least one pearlescent pigment, and at least one synthetic uncolored micronized wax.

The examples below serve to describe the invention in more detail and are not intended to be limiting in any respect. The combination possibilities below of at least one effect pigment and at least one micronized wax constitute only an exemplary selection of possible nail varnish compositions or pigment/wax mixtures.

I Preparation of the Nail Varnishes According to the Invention

EXAMPLES 1 TO 68 ACCORDING TO THE INVENTION

Phase A

| Example | INCI Name | Product name | % by weight | $D_{50}(E)/D_{50}(W)$* |
|---|---|---|---|---|
| 1 | CI 77 000 (Aluminum Powder), Silica | Visionaire Bright Silver Sea[1] | 2.00 | 1.6 |
|   |   | Ceraflour 913[2] | 5.00 |   |
| 2 | CI 77 000 (Aluminum Powder), Silica | Visionaire Bright Silver Sea | 2.00 | 1.2 |
|   |   | Ceraflour 914[2] | 5.00 |   |
| 3 | CI 77 000 (Aluminum Powder), Silica | Visionaire Sparkling Silver Sea[1] | 2.00 | 2.8 |
|   |   | Ceraflour 913 | 5.00 |   |
| 4 | CI 77 000 (Aluminum Powder), Silica | Visionaire Sparkling Silver Sea | 2.00 | 2.8 |
|   |   | Ceraflour 913 | 10.00 |   |
| 5 | CI 77 000 (Aluminum Powder), Silica | Visionaire Sparkling Silver Sea | 2.00 | 2.8 |
|   |   | Ceraflour 913 | 15.00 |   |
| 6 | CI 77 000 (Aluminum Powder), Silica | Visionaire Sparkling Silver Sea | 2.00 | 2.8 |
|   |   | Ceraflour 913 | 20.00 |   |
| 7 | CI 77 000 (Aluminum Powder), Silica | Visionaire Sparkling Silver Sea | 2.00 | 2.1 |
|   |   | Ceraflour 914 | 5.00 |   |
| 8 | CI 77 000 (Aluminum Powder), Silica | Visionaire Sparkling Silver Sea | 2.00 | 2.1 |
|   |   | Ceraflour 914 | 10.00 |   |
| 9 | CI 77 000 (Aluminum Powder), Silica | Visionaire Sparkling Silver Sea | 2.00 | 2.1 |
|   |   | Ceraflour 914 | 15.00 |   |
| 10 | CI 77 000 (Aluminum Powder), Silica | Visionaire Sparkling Silver Sea | 2.00 | 2.1 |
|   |   | Ceraflour 914 | 20.00 |   |
| 11 | CI 77 000 (Aluminum Powder), Silica | Visionaire Sparkling Silver Sea | 0.50 | 1.5 |
|   |   | Ceraflour 915[2] | 5.00 |   |
| 12 | CI 77 000 (Aluminum Powder), Silica | Visionaire Sparkling Silver Sea | 2.00 | 1.5 |
|   |   | Ceraflour 915 | 5.00 |   |
| 13 | CI 77 000 (Aluminum Powder), Silica | Visionaire Sparkling Silver Sea | 2.00 | 1.1 |
|   |   | Ceraflour 916[2] | 5.00 |   |
| 14 | CI 77 000 (Aluminum Powder), Silica | Visionaire Sparkling Silver Sea | 2.00 | 8.3 |
|   |   | Ceraflour 990[2] | 5.00 |   |
| 15 | CI 77 000 (Aluminum Powder), Silica | Visionaire Sparkling Silver Sea | 2.00 | 10.0 |
|   |   | Ceraflour 991[2] | 5.00 |   |
| 16 | CI 77 000 (Aluminum Powder), Silica Calcium Sodium Borosilicate, CI 77 891 (Titanium Dioxide), Tin Oxide | Visionaire Sparkling Silver Sea Mirage Glamour Red[1] | 1.00 1.00 | 2.8 4.3 |
|   |   | Ceraflour 913 | 5.00 |   |
| 17 | CI 77 000 (Aluminum Powder), Silica Calcium Sodium Borosilicate, CI 77 891 (Titanium Dioxide), Tin Oxide | Visionaire Sparkling Silver Sea Mirage Glamour Red | 1.00 1.00 | 2.1 3.3 |
|   |   | Ceraflour 914 | 5.00 |   |
| 18 | CI 77 000 (Aluminium Powder), Isopropyl Alcohol | Silverdream Moonlight 50IL[1] | 2.00 | 1.0 |
|   |   | Ceraflour 913 | 5.00 |   |
| 19 | CI 77 000 (Aluminium Powder), Isopropyl Alcohol | Silverdream Moonlight 50IL | 2.00 | 0.8 |
|   |   | Ceraflour 914 | 5.00 |   |
| 20 | Iron Powder, Paraffinum Liquidum (Mineral Oil) | Silverdream Polaris 90 WM[1] | 2.00 | 1.0 |
|   |   | Ceraflour 913 | 5.00 |   |
| 21 | Iron Powder, Paraffinum Liquidum (Mineral Oil) | Silverdream Polaris 90 WM | 2.00 | 1.0 |
|   |   | Ceraflour 913 | 10.00 |   |
| 22 | Iron Powder, Paraffinum Liquidum (Mineral Oil) | Silverdream Polaris 90 WM | 2.00 | 1.0 |
|   |   | Ceraflour 913 | 15.00 |   |

-continued

| Example | INCI Name | Product name | % by weight | $D_{50}(E)/D_{50}(W)$* |
|---|---|---|---|---|
| 23 | Iron Powder, Paraffinum Liquidum (Mineral Oil) | Silverdream Polaris 90 WM | 2.00 | 1.0 |
|  |  | Ceraflour 913 | 20.00 |  |
| 24 | Iron Powder, Paraffinum Liquidum (Mineral Oil) | Silverdream Polaris 90 WM | 2.00 | 0.8 |
|  |  | Ceraflour 913 | 5.00 |  |
| 25 | Iron Powder, Paraffinum Liquidum (Mineral Oil) | Silverdream Polaris 90 WM | 2.00 | 0.8 |
|  |  | Ceraflour 913 | 10.00 |  |
| 26 | Iron Powder, Paraffinum Liquidum (Mineral Oil) | Silverdream Polaris 90 WM | 2.00 | 0.8 |
|  |  | Ceraflour 913 | 15.00 |  |
| 27 | Iron Powder, Paraffinum Liquidum (Mineral Oil) | Silverdream Polaris 90 WM | 2.00 | 0.8 |
|  |  | Ceraflour 913 | 20.00 |  |
| 28 | Mica, CI 77 891 (Titanium Dioxide) | Prestige Super Soft Silver[1] | 2.00 | 0.3 |
|  |  | Ceraflour 913 | 5.00 |  |
| 29 | Mica, CI 77 891 (Titanium Dioxide) | Prestige Super Soft Silver | 2.00 | 0.2 |
|  |  | Ceraflour 914 | 5.00 |  |
| 30 | Mica, CI 77 891 (Titanium Dioxide) Polyethylene | Prestige Super Soft Silver Micropoly 250S[3] | 2.00 5.00 | 1.5 |
| 31 | Mica, CI 77 891 (Titanium Dioxide) Polyethylene/PTFE | Prestige Super Soft Silver Microsilk 418[3] | 2.00 5.00 | 0.4 |
| 32 | Mica, CI 77 891 (Titanium Dioxide) Polyethylene/PTFE | Prestige Super Soft Silver Microsilk 920[3] | 2.00 5.00 | 0.5 |
| 33 | Mica, CI 77 891 (Titanium Dioxide) PTFE | Prestige Super Soft Silver Microsilk 519[3] | 2.00 5.00 | 0.8 |
| 34 | Mica, CI 77 891 (Titanium Dioxide), Tin Oxide | Prestige Silver Star[1] | 2.00 | 1.1 |
|  |  | Ceraflour 913 | 5.00 |  |
| 35 | Mica, CI 77 891 (Titanium Dioxide), Tin Oxide | Prestige Silver Star | 2.00 | 0.8 |
|  |  | Ceraflour 914 | 5.00 |  |
| 36 | Mica, CI 77 891 (Titanium Dioxide), Tin Oxide | Prestige Sparkling Silver Star[1] | 2.00 | 3.3 |
|  |  | Ceraflour 913 | 5.00 |  |
| 37 | Mica, CI 77 891 (Titanium Dioxide), Tin Oxide | Prestige Sparkling Silver Star | 2.00 | 2.5 |
|  |  | Ceraflour 914 | 5.00 |  |
| 38 | Synthetic Flourophlogopite, CI 77 891 (Titanium Dioxide), Tin Oxide | SynCrystal Silver[1] | 2.00 | 1.2 |
|  |  | Ceraflour 913 | 5.00 |  |
| 39 | Synthetic Flourophlogopite, CI 77 891 (Titanium Dioxide), Tin Oxide | SynCrystal Silver | 2.00 | 0.9 |
|  |  | Ceraflour 914 | 5.00 |  |
| 40 | Synthetic Fluorophlogopite, CI 77 891 (Titanium Dioxide), Tin Oxide | SynCrystal Sparkling Silver[1] | 2.00 | 3.2 |
|  |  | Ceraflour 913 | 5.00 |  |
| 41 | Synthetic Fluorophlogopite, CI 77 891 (Titanium Dioxide), Tin Oxide | SynCrystal Sparkling Silver | 2.00 | 2.4 |
|  |  | Ceraflour 914 | 5.00 |  |
| 42 | Calcium Sodium Borosilicate, CI 77 891 (Titanium Dioxide), Tin Oxide | Mirage Bright Silver[1] | 2.00 | 1.8 |
|  |  | Ceraflour 913 | 5.00 |  |
| 43 | Calcium Sodium Borosilicate, CI 77 891 (Titanium Dioxide), Tin Oxide | Mirage Bright Silver | 2.00 | 1.4 |
|  |  | Ceraflour 914 | 5.00 |  |
| 44 | Calcium Sodium Borosilicate, CI 77 891 (Titanium Dioxide), Tin Oxide | Mirage Bright Silver | 2.00 | 1.0 |
|  |  | Ceraflour 915 | 1.00 |  |
| 45 | Calcium Sodium Borosilicate, CI 77 891 (Titanium Dioxide), Tin Oxide | Mirage Bright Silver | 2.00 | 1.0 |
|  |  | Ceraflour 915 | 2.00 |  |
| 46 | Calcium Sodium Borosilicate, CI 77 891 (Titanium Dioxide), Tin Oxide | Mirage Bright Silver | 2.00 | 1.0 |
|  |  | Ceraflour 915 | 3.00 |  |
| 47 | Calcium Sodium Borosilicate, CI 77 891 (Titanium Dioxide), Tin Oxide | Mirage Bright Silver | 2.00 | 1.0 |
|  |  | Ceraflour 915 | 4.00 |  |
| 48 | Calcium Sodium Borosilicate, CI 77 891 (Titanium Dioxide), Tin Oxide | Mirage Bright Silver | 2.00 | 1.0 |
|  |  | Ceraflour 915 | 5.00 |  |
| 49 | Calcium Sodium Borosilicate, CI 77 891 (Titanium Dioxide), Tin Oxide Polyethylene | Mirage Bright Silver Micropoly 250S | 2.00 5.00 | 11.0 |

-continued

| Example | INCI Name | Product name | % by weight | $D_{50}(E)/D_{50}(W)$* |
|---|---|---|---|---|
| 50 | Calcium Sodium Borosilicate, CI 77 891 (Titanium Dioxide), Tin Oxide Polethylene/PTFE | Mirage Bright Silver<br>Microsilk 418 | 2.00<br>5.00 | 3.0 |
| 51 | Calcium Sodium Borosilicate, CI 77 891 (Titanium Dioxide), Tin Oxide Polypropylene/PTFE | Mirage Bright Silver<br>Microsilk 920 | 2.00<br>5.00 | 3.7 |
| 52 | Calcium Sodium Borosilicate, CI 77 891 (Titanium Dioxide), Tin Oxide PTFE | Mirage Bright Silver<br>Microslip 519 | 2.00<br>5.00 | 6.0 |
| 53 | Calcium Sodium Borosilicate, CI 77 891 (Titanium Dioxide), Tin Oxide | Mirage Bright Blue[1)]<br>Ceraflour 913 | 2.00<br>5.00 | 1.7 |
| 54 | Calcium Sodium Borosilicate, CI 77 891 (Titanium Dioxide), Tin Oxide | Mirage Bright Blue<br>Ceraflour 914 | 2.00<br>5.00 | 1.3 |
| 55 | Calcium Sodium Borosilicate, CI 77 891 (Titanium Dioxide), Tin Oxide | Mirage Sparkling Silver[1)]<br>Ceraflour 913 | 2.00<br>5.00 | 3.2 |
| 56 | Calcium Sodium Borosilicate, CI 77 891 (Titanium Dioxide), Tin Oxide | Mirage Sparkling Silver<br>Ceraflour 913 | 2.00<br>7.00 | 3.2 |
| 57 | Calcium Sodium Borosilicate, CI 77 891 (Titanium Dioxide), Tin Oxide | Mirage Sparkling Silver<br>Ceraflour 913 | 2.00<br>10.00 | 3.2 |
| 58 | Calcium Sodium Borosilicate, CI 77 891 (Titanium Dioxide), Tin Oxide | Mirage Sparkling Silver<br>Ceraflour 913 | 2.00<br>15.00 | 3.2 |
| 59 | Calcium Sodium Borosilicate, CI 77 891 (Titanium Dioxide), Tin Oxide | Mirage Sparkling Silver<br>Ceraflour 914 | 2.00<br>5.00 | 2.4 |
| 60 | Calcium Sodium Borosilicate, CI 77 891 (Titanium Dioxide), Tin Oxide | Mirage Sparkling Silver<br>Ceraflour 914 | 2.00<br>7.00 | 2.4 |
| 61 | Calcium Sodium Borosilicate, CI 77 891 (Titanium Dioxide), Tin Oxide | Mirage Sparkling Silver<br>Ceraflour 914 | 2.00<br>10.00 | 2.4 |
| 62 | Calcium Sodium Borosilicate, CI 77 891 (Titanium Dioxide), Tin Oxide | Mirage Sparkling Silver<br>Ceraflour 914 | 2.00<br>15.00 | 2.4 |
| 63 | Calcium Sodium Borosilicate, CI 77 891 (Titanium Dioxide), CI 77 492 (Iron Oxides), Silica, Tin Oxide | Mirage Sparkling Luxury Gold[1)]<br>Ceraflour 913 | 2.00<br>5.00 | 2.9 |
| 64 | Calcium Sodium Borosilicate, CI 77 891 (Titanium Dioxide), CI 77 492 (Iron Oxides), Silica, Tin Oxide | Mirage Sparkling Luxury Gold<br>Ceraflour 914 | 2.00<br>5.00 | 2.2 |
| 65 | Calcium Sodium Borosilicate, CI 77 891 (Titanium Dioxide), Tin Oxide | Mirage Glamour Silver[1)]<br>Ceraflour 913 | 2.00<br>5.00 | 4.9 |
| 66 | Calcium Sodium Borosilicate, CI 77 891 (Titanium Dioxide), Tin Oxide | Mirage Glamour Silver<br>Ceraflour 914 | 2.00<br>5.00 | 3.7 |
| 67 | Calcium Sodium Borosilicate, CI 77 891 (Titanium Dioxide), Tin Oxide | Mirage Twinkling Silver[1)]<br>Ceraflour 913 | 2.00<br>5.00 | 11.7 |
| 68 | Calcium Sodium Borosilicate, CI 77 891 (Titanium Dioxide), Tin Oxide | Mirage Twinkling Silver<br>Ceraflour 914 | 2.00<br>5.00 | 8.8 |

*$D_{50}$ (E)/$D_{50}$ (W) corresponds to formula (I), where (E) is effect pigment, (W) is micronized wax:

$$\frac{D_{50} \text{ effect pigment}}{D_{50} \text{ micronized wax}} \quad (I)$$

1) Manufacturer/supplier: Eckart

| Effect pigment | $D_{50}$ (μm) |
|---|---|
| Visionaire Bright Silver Sea | 29 |
| Visionaire Sparkling Silver Sea | 50 |

-continued

| Effect pigment | $D_{50}$ (μm) |
|---|---|
| Mirage Glamour Red | 78 |
| Silverdream Moonlight 50 IL | 18 |
| Silverdream Polaris 90 WM | 18 |
| Prestige Super Soft Silver | 4.5 |
| Prestige Silver Star | 20 |
| Prestige Sparkling Silver Star | 59 |
| SynCrystal Silver | 22 |
| SynCrystal Sparkling Silver | 58 |
| Mirage Bright Silver | 33 |

-continued

| Effect pigment | $D_{50}$ (μm) |
|---|---|
| Mirage Bright Blue | 31 |
| Mirage Sparkling Silver | 58 |
| Mirage Sparkling Luxury Gold | 52 |
| Mirage Glamour Silver | 89 |
| Mirage Twinkling Silver | 210 |

2) Manufacturer/supplier: BYK-Chemie

| Micronized wax | $D_{50}$ (μm) |
|---|---|
| Ceraflour 913 | 18 |
| Ceraflour 914 | 24 |
| Ceraflour 915 | 34 |
| Ceraflour 916 | 46 |
| Ceraflour 990 | 6 |
| Ceraflour 991 | 5 |

3) Manufacturer: Micro Powders

| Micronized wax | $D_{50}$ (μm) |
|---|---|
| Micropoly 250S | 2.0-4.0 |
| Microsilk 418 | 10.0-12.0 |
| Microsilk 920 | 7.0-11.0 |
| Microslip 519 | 5.0-6.0 |

Phase B a) Commercially Available Nail Varnish Base

| INCI Name | Product name | % by weight | Manufacturer/Supplier |
|---|---|---|---|
| Butyl Acetate, Ethyl Acetate, Nitrocellulose, Isopropyl Alcohol | International Lacquers Nailpolish & Care Base 359 | ad 100.00 | International Lacquers | b) Alternatively, phase B can be prepared from for example the following constituents;

| INCI Name | Product name | % by weight | Manufacturer/Supplier |
|---|---|---|---|
| Phase A' | | | |
| Butyl Acetate | n-Butyl acetate | 34 | VWR |
| Ethyl Acetate | Ethyl acetate | 20 | VWR |
| Nitrocellulose, Isopropyl Alcohol | Walsroder Nitrocellulose E400 Isopropanol 30% | 23 | Dow Wolff Cellulosics |
| Phase B' | | | |
| Toluenesulfonamide, n-Butyl Acetate | Ketjenflex MS80 | 10 | Axcentive |
| Isopropyl Alcohol | 2-Propanol | 5 | VWR |
| Acetyl Tributyl Citrate | Tributylacetyl citrate | 7 | VWR |
| Silica | Aerosil 200 | 1 | Evonik |

Phase A' and phase B' were mixed separately and then poured into a suitable vessel.

c) Phase B can also be an aqueous nail varnish base according to WO 2007/115675 A2 example 1.

Optional Phase C

The nail varnish base was colored, depending on the desired optical effect, with at least one of the following dyes Blanc Covachip W 9705 ET, Jaune Covachip W 1701 ET, Orange Covachip W 2702 ET, Rouge Covachip W 3714 ET, Cerise Covachip W 4702 ET, Rubis Covachip W 4705 ET, Rubis Covachip W 4700 ET, Bleu Covachip W 6709 ET, Brun Covachip W 8700 ET or Noir Covachip W 9701 ET (LCW), which was added to the combined phases A and B in the form of a 10% strength by weight dispersion. Phase C, the 10% strength by weight dispersion, consists of 10% by weight of "Covachip", 20% by weight of butyl acetate, 70% by weight of nail varnish base (phase B). The optional phase C can be used in the nail varnish according to the invention in a range from 0.1 to 10% by weight, based on the total weight of the nail varnish. The amount of nail varnish base (phase B) must then be adapted accordingly.

To produce the nail varnish according to the invention, phase A and phase B and also optionally phase C were mixed together and then poured into a nail varnish container. The optionally present phase C here can either be mixed firstly with phase B or added to the combined phases A and B.

The micronized wax can be used in the nail varnish according to the invention in a range from 0.1 to 25% by weight, preferably in a range from 1.0 to 20% by weight, in each case based on the total weight of the nail varnish. In combination with effect pigments, the micronized wax is used preferably in a range from 1 to 15% by weight, particularly preferably in a range from 3 to 10% by weight, in each case based on the total weight of the nail varnish. Variations of this kind can be evened out by means of a corresponding increase or reduction in the nail varnish base (phase B) used.

Organic and inorganic pigments can be added to the nail varnish according to the invention in a range from 0.05 to 2.5% by weight, preferably in a range from 0.05 to 1.0% by weight and particularly preferably in a range from 0.07 to 0.5% by weight, in each case based on the total weight of the nail varnish according to the invention. Organic and inorganic pigments are preferably added in the form of dispersions to the nail varnish according to the invention. The composition of such dispersions is described by way of example for phase C.

The effect pigments are used in the nail varnish according to the invention preferably in a range from 0.05 to 6.0% by weight, particularly preferably in a range from 0.1 to 5.0% by weight, further preferably in a range from 0.15 to 4.0% by weight and very particularly preferably in a range from 0.2 to 3.5% by weight, in each case based on the total weight of the nail varnish according to the invention. These variations can also be evened out by means of a corresponding increase or reduction in the nail varnish base used.

Ia Preparation of the Pigment/Wax Mixtures According to the Invention

| Example | INCI Name | Product name | % by weight |
|---|---|---|---|
| 69 | | Ceraflour 913 | 70.00 |
| | Calcium Sodium Borosilicate, CI 77 891 (Titanium Dioxide), Tin Oxide | Mirage Bright Silver | 30.00 |

-continued

| Example | INCI Name | Product name | % by weight |
|---|---|---|---|
| 70 | Calcium Sodium Borosilicate, CI 77 891 (Titanium Dioxide), Tin Oxide | Ceraflour 914 Mirage Bright Silver | 70.00 30.00 |

To produce the pigment/wax mixture according to the invention, the pigment and the micronized wax were introduced as initial charge in a plastic beaker and then homogenized in a speed mixer (Hauschild) for 30 s at 2000 rpm.

This pigment/wax mixture can be incorporated into a standard commercial nail varnish base (e.g. phase B).

| Product name/Example | % by weight |
|---|---|
| Example 69 or 70 | 7.70 |
| International Lacquers Nailpolish & Care Base 359 | 92.30 |

COMPARATIVE EXAMPLES 1 TO 32

Phase A

| Comparative example | INCI Name | Product name | % by weight |
|---|---|---|---|
| 1 | CI 77 000 (Aluminum Powder), Silica | Visionaire Bright Silver Sea | 2.00 |
| 2 | CI 77 000 (Aluminum Powder), Silica | Visionaire Bright Silver Sea | 2.00 |
|   | Talc | Talc[4] | 20.00 |
| 3 | CI 77 000 (Aluminum Powder), Silica | Visionaire Sparkling Silver Sea | 2.00 |
| 4 | CI 77 000 (Aluminum Powder), Silica | Visionaire Sparkling Silver Sea | 2.00 |
|   | Talc | Talc | 5.00 |
| 5 | CI 77 000 (Aluminum Powder), Silica | Visionaire Sparkling Silver Sea | 2.00 |
|   | Talc | Talc | 10.00 |
| 6 | CI 77 000 (Aluminum Powder), Silica | Visionaire Sparkling Silver Sea | 2.00 |
|   | Talc | Talc | 15.00 |
| 7 | CI 77 000 (Aluminum Powder), Silica | Visionaire Sparkling Silver Sea | 2.00 |
|   | Talc | Talc | 20.00 |
| 8 | CI 77 000 (Aluminum Powder), Silica | Visionaire Sparkling Silver Sea | 1.00 |
|   | Calcium Sodium Borosilicate, CI 77 891 (Titanium Dioxide), Tin Oxide | Mirage Glamour Red | 1.00 |
| 9 | CI 77 000 (Aluminum Powder), Silica | Visionaire Sparkling Silver Sea | 1.00 |
|   | Calcium Sodium Borosilicate, CI 77 891 (Titanium Dioxide), Tin Oxide | Mirage Glamour Red | 1.00 |
|   | Talc | Talc | 20.00 |
| 10 | CI 77 000 (Aluminum Powder), Isopropyl Alcohol | Silverdream Moonlight 50IL | 2.00 |
| 11 | CI 77 000 (Aluminum Powder), Isopropyl Alcohol | Silverdream Moonlight 50IL | 2.00 |
|   | Talc | Talc | 20.00 |
| 12 | Iron Powder, Paraffinum Liquidum (Mineral Oil) | Silverdream Polaris 90 WM | 2.00 |
| 13 | Iron Powder, Paraffinum Liquidum (Mineral Oil) | Silverdream Polaris 90 WM | 2.00 |
|   | Talc | Talc | 5.00 |
| 14 | Iron Powder, Paraffinum Liquidum (Mineral Oil) | Silverdream Polaris 90 WM | 2.00 |
|   | Talc | Talc | 10.00 |
| 15 | Iron Powder, Paraffinum Liquidum (Mineral Oil) | Silverdream Polaris 90 WM | 2.00 |
|   | Talc | Talc | 15.00 |
| 16 | Iron Powder, Paraffinum Liquidum (Mineral Oil) | Silverdream Polaris 90 WM | 2.00 |
|   | Talc | Talc | 20.00 |
| 17 | Mica, CI 77 891 (Titanium Dioxide) | Prestige Super Soft Silver | 2.00 |
| 18 | Mica, CI 77 891 (Titanium Dioxide) | Prestige Super Soft Silver | 2.00 |
|   | Polyethylene | Microscrub 20PC[3] | 5.00 |
| 19 | Mica, CI 77 891 (Titanium Dioxide), Tin Oxide | Prestige Silver Star | 2.00 |
| 20 | Mica, CI 77 891 (Titanium Dioxide), Tin Oxide | Prestige Sparkling Silver Star | 2.00 |
| 21 | Synthetic Flourophlogopite, CI 77 891 (Titanium Dioxide), Tin Oxide | SynCrystal Silver | 2.00 |
| 22 | Synthetic Fluorophlogopite, CI 77 891 (Titanium Dioxide), Tin Oxide | SynCrystal Silver | 2.00 |
|   | Talc | Talc | 20.00 |

-continued

| Comparative example | INCI Name | Product name | % by weight |
|---|---|---|---|
| 23 | Synthetic Flourophlogopite, CI 77 891 (Titanium Dioxide), Tin Oxide | SynCrystal Sparkling Silver | 2.00 |
| 24 | Synthetic Flourophlogopite, CI 77 891 (Titanium Dioxide), Tin Oxide | SynCrystal Sparkling Silver | 2.00 |
|  | Talc | Talc | 20.00 |
| 25 | Calcium Sodium Borosilicate, CI 77 891 (Titanium Dioxide), Tin Oxide | Mirage Bright Silver | 2.00 |
| 26 | Calcium Sodium Borosilicate, CI 77 891 (Titanium Dioxide), Tin Oxide | Mirage Bright Silver | 2.00 |
|  | Polyethylene | Microscrub 20PC | 5.00 |
| 27 | Calcium Sodium Borosilicate, CI 77 891 (Titanium Dioxide), Tin Oxide | Mirage Bright Blue | 2.00 |
| 28 | Calcium Sodium Borosilicate, CI 77 891 (Titanium Dioxide), Tin Oxide | Mirage Bright Blue | 2.00 |
|  | Talc | Talc | 20.00 |
| 29 | Calcium Sodium Borosilicate, CI 77 891 (Titanium Dioxide), Tin Oxide | Mirage Sparkling Silver | 2.00 |
| 30 | Calcium Sodium Borosilicate, CI 77 891 (Titanium Dioxide), CI 77 492 (Iron Oxides), Silica, Tin Oxide | Mirage Sparkling Luxury Gold | 2.00 |
| 31 | Calcium Sodium Borosilicate, CI 77 891 (Titanium Dioxide), Tin Oxide | Mirage Glamour Silver | 2.00 |
| 32 | Calcium Sodium Borosilicate, CI 77 891 (Titanium Dioxide), Tin Oxide | Mirage Twinkling Silver | 2.00 |

[3]Manufacturer/supplier: Micro Powders (Microscrub 20PC mesh size maximum 20, corresponds to ca. 841 μm)
[4]Manufacturer/supplier: BDH Prolabo ($D_{50}$ = 18 μm)

Phase B

| INCI Name | Product name | % by weight | Manufacturer/ Supplier |
|---|---|---|---|
| Butyl Acetate, Ethyl Acetate, Nitrocellulose, Isopropyl Alcohol | International Lacquers Nailpolish & Care Base 359 | ad 100 | International Lacquers |

Optionally phase C, analogously to phase C of the examples according to the invention.

To produce the nail varnish according to the invention, phase A and phase B and also optionally phase C were mixed together and then poured into a nail varnish container.

Micronized waxes with an average particle size >200 μm are less suitable for use in the nail varnish according to the invention. The micronized wax Microscrub 20PC used in comparative example 18 was perceived optically as an incorrect coating in the nail varnish application since the coarse particles produce a very inhomogeneous and unattractive appearance. In terms of feel, this nail varnish application was perceived as being unpleasant.

II Characterization of the Pigments and Micronized Waxes Used

IIa Particle Size Measurement

The size distribution curve of the pearlescent pigments and micronized waxes was determined using an instrument from Malvern (instrument: Malvern Mastersizer 2000) in accordance with the manufacturer's instructions. For this purpose, ca. 0.1 g of the corresponding micronized wax or pearlescent pigment was added to the sample preparation cell of the instrument as aqueous suspension, without the addition of dispersion auxiliaries, with constant stirring by means of a Pasteur pipette and measured several times. The resulting average values were formed from the individual measurement results. The scattered-light signals were evaluated here by the Fraunhofer method. The size distribution curve of the metal effect pigments (in powder form) was determined using an instrument from Sympatec (instrument: Helos particle size analysis with Rodos dry dispersion and Vibri feeder) in accordance with the manufacturer's instructions. For this purpose, ca. 5 to 25 cm³ of powder were added to the feeder depending on the nature of the metal effect pigment to be measured. After the start of the measurement operation, metering, dry dispersion and measurement of the sample by laser diffraction then take place automatically. The scattered-light signals were evaluated here by the Fraunhofer method.

The size distribution curve of the metal effect pigments (in paste form), of the organic and inorganic pigments was measured using an instrument from Quantachrome (instrument: Cilas 1064) in accordance with the manufacturer's instructions. For this purpose, ca. 50 ml of the corresponding pigment were suspended in isopropanol, treated for 300 seconds in an ultrasound bath (instrument: Sonorex IK 52, Bandelin) and then added by means of a Pasteur pipette to the sample preparation cell of the instrument and measured several times. The resulting average values were formed from the individual measurement results. The scattered-light signals were evaluated here by the Fraunhofer method (metal effect pigments) or the Mie theory (organic and inorganic pigments).

Within the context of this invention, the average size $D_{50}$ is understood as meaning the $D_{50}$ value of the cumulative frequency distribution of the volume-averaged size distribution function as are obtained by laser diffraction methods. The $D_{50}$ value indicates that 50% of the micronized waxes or pigments have a diameter which is less than or equal to the stated value, for example 20 μm.

Accordingly, the $D_{90}$ value indicates that 90% of the micronized waxes or pigments have a diameter which is less than or equal to the particular value.

Furthermore, the $D_{10}$ value indicates that 10% of the micronized waxes or pigments have a diameter which is less than or equal to the particular value.

IIb Determination of the Melting Range of the Micronized Waxes

The melting range was determined using a melting point measuring device (model 5A 6797, Gallenkamp). The method corresponded to the DGF standard method C-IV 3a.

| Micronized wax | Melting range (° C.) |
| --- | --- |
| Ceraflour 913 | 158-160 |
| Ceraflour 914 | 156-160 |
| Micropoly 250S | 129-130 |
| Microsilk 418 | 116-118 |

III Characterization of the Optical Effect of the Nail Varnishes According to the Invention IIIa Determination of the Light/Dark Flop (Flop Index)

The light/dark flop (flop index) of nail varnishes provided with effect pigments was ascertained by reference to nail varnish applications on black-white coverage cards (chart PA-2812, BYK-Gardner) using the BYK-mac instrument (BYK-Gardner). The nail varnishes here were applied manually to the black-white coverage cards (wet film thickness 120 µm) using an Erichsen Film Applicator (System Wasag, model 288, Erichsen). The flop index is defined in accordance with Alman as follows (S. Schellenberger, M. Entenmann, A. Hennemann, P. Thometzek, Farbe and Lack, 04/2007, p. 130):

$$\text{Flop index} = 2.69 \cdot (L_{E1} - L_{E3})^{1.11} / L_{E2}^{0.86}$$

where $L_{E1}$ is the brightness of the near-specular measuring angle (E1=15° relative to the specular angle), $L_{E2}$ is the brightness of the measuring angle between near-specular and far-specular angle (E2=45° relative to the specular angle) and $L_m$ is the brightness of the far-specular measuring angle (E3=110° relative to the specular angle).

The values listed in Table 2 were measured on the black substrate of the black-white coverage card. In Table 2, only phase A of the nail varnishes is described; the commercially available nail varnish base International Lacquers Nailpolish & Care Base 359 (ad 1001 by weight) was used, as described above, as phase B.

TABLE 2

| | Brightness L* and flop index | | | | |
| --- | --- | --- | --- | --- | --- |
| Example/comparative example | Product name | % by weight | Measurement geometry (°) | L* | Flop Index |
| Comparative example 1 | Visionaire Bright Silver Sea | 2.00 | −15 | 139.5 | 23.5 |
| | | | 15 | 119.2 | |
| | | | 25 | 72.9 | |
| | | | 45 | 32.5 | |
| | | | 75 | 17.8 | |
| | | | 110 | 14.5 | |
| Example 1 | Visionaire Bright Silver Sea | 2.00 | −15 | 97.7 | 7.1 |
| | | | 15 | 86.8 | |
| | | | 25 | 73.1 | |
| | Ceraflour 913 | 5.00 | 45 | 53.3 | |
| | | | 75 | 40.7 | |
| | | | 110 | 34.7 | |
| Example 2 | Visionaire Bright Silver Sea | 2.00 | −15 | 99.7 | 7.1 |
| | | | 15 | 89.0 | |
| | | | 25 | 73.3 | |
| | Ceraflour 914 | 5.00 | 45 | 53.5 | |
| | | | 75 | 41.6 | |
| | | | 110 | 36.8 | |
| Comparative example 2 | Visionaire Bright Silver Sea | 2.00 | −15 | 99.2 | 5.7 |
| | | | 15 | 88.8 | |
| | | | 25 | 79.9 | |
| | Talc | 20.00 | 45 | 61.5 | |
| | | | 75 | 46.6 | |
| | | | 110 | 40.7 | |
| Comparative example 3 | Visionaire Sparkling Silver Sea | 2.00 | −15 | 130.6 | 26.2 |
| | | | 15 | 108.4 | |
| | | | 25 | 60.5 | |
| | | | 45 | 25.8 | |
| | | | 75 | 14.3 | |
| | | | 110 | 12.1 | |
| Example 3 | Visionaire Sparkling Silver Sea | 2.00 | −15 | 110.0 | 7.5 |
| | | | 15 | 98.1 | |
| | | | 25 | 84.0 | |
| | Ceraflour 913 | 5.00 | 45 | 61.0 | |
| | | | 75 | 43.9 | |
| | | | 110 | 36.9 | |
| Example 4 | Visionaire Sparkling Silver Sea | 2.00 | −15 | 85.7 | 3.8 |
| | | | 15 | 76.9 | |
| | | | 25 | 70.5 | |
| | Ceraflour 913 | 10.00 | 45 | 57.5 | |
| | | | 75 | 48.8 | |
| | | | 110 | 45.7 | |
| Example 5 | Visionaire Sparkling Silver Sea | 2.00 | −15 | 84.3 | 1.3 |
| | | | 15 | 77.2 | |
| | | | 25 | 72.9 | |
| | Ceraflour 913 | 15.00 | 45 | 65.1 | |
| | | | 75 | 62.7 | |
| | | | 110 | 63.8 | |

TABLE 2-continued

Brightness L* and flop index

| Example/comparative example | Product name | % by weight | Measurement geometry (°) | L* | Flop Index |
|---|---|---|---|---|---|
| Example 6 | Visionaire Sparkling Silver Sea | 2.00 | −15 | 85.3 | 0.7 |
|  |  |  | 15 | 79.4 |  |
|  |  |  | 25 | 76.2 |  |
|  | Ceraflour 913 | 20.00 | 45 | 70.3 |  |
|  |  |  | 75 | 69.7 |  |
|  |  |  | 110 | 71.1 |  |
| Example 7 | Visionaire Sparkling Silver Sea | 2.00 | −15 | 109.2 | 8.1 |
|  |  |  | 15 | 97.2 |  |
|  |  |  | 25 | 80.9 |  |
|  | Ceraflour 914 | 5.00 | 45 | 58.0 |  |
|  |  |  | 75 | 40.3 |  |
|  |  |  | 110 | 34.5 |  |
| Example 8 | Visionaire Sparkling Silver Sea | 2.00 | −15 | 83.8 | 2.6 |
|  |  |  | 15 | 74.8 |  |
|  |  |  | 25 | 69.1 |  |
|  | Ceraflour 914 | 10.00 | 45 | 58.6 |  |
|  |  |  | 75 | 52.4 |  |
|  |  |  | 110 | 51.9 |  |
| Example 9 | Visionaire Sparkling Silver Sea | 2.00 | −15 | 86.5 | 1.7 |
|  |  |  | 15 | 77.9 |  |
|  |  |  | 25 | 72.8 |  |
|  | Ceraflour 914 | 15.00 | 45 | 63.7 |  |
|  |  |  | 75 | 60.2 |  |
|  |  |  | 110 | 61.4 |  |
| Example 10 | Visionaire Sparkling Silver Sea | 5.00 | −15 | 94.6 | 1.8 |
|  |  |  | 15 | 84.7 |  |
|  |  |  | 25 | 78.7 |  |
|  | Ceraflour 914 | 20.00 | 45 | 68.4 |  |
|  |  |  | 75 | 64.9 |  |
|  |  |  | 110 | 66.3 |  |
| Comparative example 4 | Visionaire Sparkling Silver Sea | 2.00 | −15 | 144.0 | 21.9 |
|  |  |  | 15 | 121.7 |  |
|  |  |  | 25 | 78.3 |  |
|  | Talc | 5.00 | 45 | 35.8 |  |
|  |  |  | 75 | 19.3 |  |
|  |  |  | 110 | 16.0 |  |
| Comparative example 5 | Visionaire Sparkling Silver Sea | 2.00 | −15 | 134.5 | 15.8 |
|  |  |  | 15 | 116.3 |  |
|  |  |  | 25 | 85.0 |  |
|  | Talc | 10.00 | 45 | 45.0 |  |
|  |  |  | 75 | 26.0 |  |
|  |  |  | 110 | 22.1 |  |
| Comparative example 6 | Visionaire Sparkling Silver Sea | 2.00 | −15 | 121.2 | 10.8 |
|  |  |  | 15 | 106.3 |  |
|  |  |  | 25 | 85.9 |  |
|  | Talc | 15.00 | 45 | 53.5 |  |
|  |  |  | 75 | 33.8 |  |
|  |  |  | 110 | 29.8 |  |
| Comparative example 7 | Visionaire Sparkling Silver Sea | 2.00 | −15 | 110.2 | 6.9 |
|  |  |  | 15 | 100.4 |  |
|  |  |  | 25 | 87.8 |  |
|  | Talc | 20.00 | 45 | 63.2 |  |
|  |  |  | 75 | 46.6 |  |
|  |  |  | 110 | 42.5 |  |
| Comparative example 8 | Visionaire Sparkling Silver Sea | 1.00 | −15 | 112.5 | 25.8 |
|  |  |  | 15 | 92.4 |  |
|  |  |  | 25 | 51.5 |  |
|  | Mirage Glamour Red | 1.00 | 45 | 21.5 |  |
|  |  |  | 75 | 12.0 |  |
|  |  |  | 110 | 9.8 |  |
| Example 16 | Visionaire Sparkling Silver Sea | 1.00 | −15 | 93.6 | 8.1 |
|  |  |  | 15 | 81.3 |  |
|  | Mirage Glamour Red | 1.00 | 25 | 67.7 |  |
|  |  |  | 45 | 46.7 |  |
|  | Ceraflour 913 | 5.00 | 75 | 33.0 |  |
|  |  |  | 110 | 28.4 |  |
| Example 17 | Visionaire Sparkling Silver Sea | 1.00 | −15 | 94.9 | 8.2 |
|  |  |  | 15 | 82.5 |  |
|  | Mirage Glamour Red | 1.00 | 25 | 67.0 |  |
|  |  |  | 45 | 46.2 |  |
|  | Ceraflour 914 | 5.00 | 75 | 32.6 |  |
|  |  |  | 110 | 29.2 |  |

TABLE 2-continued

| Brightness L* and flop index | | | | | |
|---|---|---|---|---|---|
| Example/comparative example | Product name | % by weight | Measurement geometry (°) | L* | Flop Index |
| Comparative example 9 | Visionaire Sparkling Silver Sea | 1.00 | −15 | 97.8 | 6.8 |
| | | | 15 | 86.7 | |
| | Mirage Glamour Red | 1.00 | 25 | 75.2 | |
| | | | 45 | 53.8 | |
| | Talc | 20.00 | 75 | 39.7 | |
| | | | 110 | 36.2 | |
| Comparative example 10 | Silverdream Moonlight 50IL | 2.00 | −15 | 173.1 | 28.7 |
| | | | 15 | 149.9 | |
| | | | 25 | 86.6 | |
| | | | 45 | 35.0 | |
| | | | 75 | 22.0 | |
| | | | 110 | 17.3 | |
| Example 18 | Silverdream Moonlight 50IL | 2.00 | −15 | 113.9 | 5.3 |
| | | | 15 | 103.7 | |
| | | | 25 | 90.2 | |
| | Ceraflour 913 | 5.00 | 45 | 71.0 | |
| | | | 75 | 59.8 | |
| | | | 110 | 53.4 | |
| Example 19 | Silverdream Moonlight 50IL | 2.00 | −15 | 120.7 | 6.4 |
| | | | 15 | 110.5 | |
| | | | 25 | 90.3 | |
| | Ceraflour 914 | 5.00 | 45 | 68.0 | |
| | | | 75 | 57.3 | |
| | | | 110 | 53.0 | |
| Comparative example 11 | Silverdream Moonlight 50IL | 2.00 | −15 | 115.6 | 5.3 |
| | | | 15 | 104.7 | |
| | | | 25 | 95.6 | |
| | Talc | 20.00 | 45 | 76.7 | |
| | | | 75 | 60.4 | |
| | | | 110 | 51.2 | |
| Comparative example 21 | SynCrystal Silver | 2.00 | −15 | 112.9 | 24.0 |
| | | | 15 | 95.7 | |
| | | | 25 | 54.5 | |
| | | | 45 | 24.2 | |
| | | | 75 | 14.2 | |
| | | | 110 | 11.0 | |
| Example 38 | SynCrystal Silver | 2.00 | −15 | 85.0 | 5.9 |
| | | | 15 | 74.8 | |
| | | | 25 | 64.4 | |
| | Ceraflour 913 | 5.00 | 45 | 47.9 | |
| | | | 75 | 38.4 | |
| | | | 110 | 34.0 | |
| Example 39 | SynCrystal Silver | 2.00 | −15 | 87.5 | 6.2 |
| | | | 15 | 76.9 | |
| | | | 25 | 64.2 | |
| | Ceraflour 914 | 5.00 | 45 | 47.3 | |
| | | | 75 | 38.6 | |
| | | | 110 | 34.9 | |
| Comparative example 22 | SynCrystal Silver | 2.00 | −15 | 90.5 | 5.1 |
| | | | 15 | 79.5 | |
| | | | 25 | 71.9 | |
| | Talc | 20.00 | 45 | 55.5 | |
| | | | 75 | 43.9 | |
| | | | 110 | 39.8 | |
| Comparative example 23 | SynCrystal Sparkling Silver | 2.00 | −15 | 91.1 | 24.9 |
| | | | 15 | 74.4 | |
| | | | 25 | 40.2 | |
| | | | 45 | 16.9 | |
| | | | 75 | 10.1 | |
| | | | 110 | 7.8 | |
| Example 40 | SynCrystal Sparkling Silver | 2.00 | −15 | 82.9 | 7.5 |
| | | | 15 | 71.9 | |
| | | | 25 | 61.2 | |
| | Ceraflour 913 | 5.00 | 45 | 42.2 | |
| | | | 75 | 30.5 | |
| | | | 110 | 26.3 | |

TABLE 2-continued

Brightness L* and flop index

| Example/comparative example | Product name | % by weight | Measurement geometry (°) | L* | Flop Index |
|---|---|---|---|---|---|
| Example 41 | SynCrystal Sparkling Silver | 2.00 | −15 | 84.4 | 7.7 |
| | | | 15 | 73.6 | |
| | | | 25 | 61.6 | |
| | Ceraflour 914 | 5.00 | 45 | 42.4 | |
| | | | 75 | 30.2 | |
| | | | 110 | 26.7 | |
| Comparative example 24 | SynCrystal Sparkling Silver | 2.00 | −15 | 88.8 | 6.7 |
| | | | 15 | 77.7 | |
| | | | 25 | 66.9 | |
| | Talc | 20.00 | 45 | 46.8 | |
| | | | 75 | 35.3 | |
| | | | 110 | 33.0 | |
| Comparative example 27 | Mirage Bright Blue | 2.00 | −15 | 71.8 | 22.3 |
| | | | 15 | 56.4 | |
| | | | 25 | 31.1 | |
| | | | 45 | 12.9 | |
| | | | 75 | 9.1 | |
| | | | 110 | 7.7 | |
| Example 53 | Mirage Bright Blue | 2.00 | −15 | 60.0 | 6.4 |
| | | | 15 | 46.0 | |
| | | | 25 | 36.8 | |
| | Ceraflour 913 | 5.00 | 45 | 25.2 | |
| | | | 75 | 21.0 | |
| | | | 110 | 19.6 | |
| Example 54 | Mirage Bright Blue | 2.00 | −15 | 60.5 | 6.4 |
| | | | 15 | 46.8 | |
| | | | 25 | 37.1 | |
| | Ceraflour 914 | 5.00 | 45 | 25.4 | |
| | | | 75 | 21.5 | |
| | | | 110 | 20.2 | |
| Comparative example 28 | Mirage Bright Blue | 2.00 | −15 | 66.1 | 4.4 |
| | | | 15 | 50.6 | |
| | | | 25 | 44.7 | |
| | Talc | 20.00 | 45 | 33.1 | |
| | | | 75 | 27.2 | |
| | | | 110 | 27.0 | |

The greater the numerical value of the flop index, the greater the expression of light/dark flop. The nail varnishes according to the invention have a clearly lower flop index in the applications. When comparing the flop index values of the applications of a nail varnish pigmented with the metal effect pigment Visionaire Sparkling Silver Sea without micronized wax and in the presence of at least one micronized wax, a reduction in the flop index of 26.2 (comparative example 3) by ca. 18 units to 7.5 (example 3) or 8.1 (example 7) can be seen.

If, instead of the at least one micronized wax for achieving a weakly pronounced light/dark flop (low numerical value of the flop index) in the applied nail varnish, a standard commercial matting agent such as, for example, talc were used, then a significantly larger amount of matting agent would have to be added to achieve a comparable optical effect. Whereas the presence of 5% by weight of at least one micronized wax already brought about a significant reduction in the flop index, in the presence of 5% by weight of talc, a significant light/dark flop with a correspondingly high value of the flop index of 21.9 was still observed (comparative example 4). The addition of 10% by weight of talc reduced this value to 15.8 (comparative example 5), but only by adding 15% by weight of talc could a flop index of 10.8 be achieved (comparative example 6). In order to thus achieve an optical effect comparable with that achieved by adding 5% by weight of micronized wax, at least 15% by weight of talc had to be used (comparative example 6). When adding 20% by weight of talc, finally, a flop index of the applied nail varnish of 6.9 was measured (comparative example 7).

IIIb Shine Measurements

The shine measurements were carried out by reference to nail varnish applications on black-white coverage cards (chart PA-2812, BYK-Gardner) using the instrument micro-TRI-gloss μ (BYK-Gardner) in accordance with the manufacturer's instructions at a measurement geometry of 20° and 60°, relative to the perpendicular, in each case on white and black substrate. Here, the nail varnishes were applied manually to the black-white coverage cards (wet film thickness 120 μm) using an Erichsen Film Applicator (System Wasag, model 288, Erichsen) and dried at room temperature. A measurement geometry of 60° is suitable for the so-called "medium shine" in the range from 10 to 70 shine points, with a higher numerical value for the shine points corresponding to a higher shine. A measurement geometry of 20° is suitable for the so-called "high shine", i.e. if the shine value at the measurement geometry of 60° is above 70 shine points, then measurement is carried out at a measurement geometry of 20° (BYK-Gardner, catalog "Qualitäskontrolle für Lacke and Kunststoffe [Quality control for coatings and plastics]" 2011/2012, p. 16). The shine values listed below in Table 3 are average values from five individual measurements in each case. In Table 3, for the sake of simplicity, only phase A of the nail varnishes is listed; the commercially available nail varnish base International Lacquers Nailpolish & Care Base 359 (ad 100% by weight) was used, as described above, as phase B.

TABLE 3

Shine values of nail varnish applications at 20° and 60°

| Example/comparative example | Product name | % by weight | Shine (white) 20° | Shine (white) 60° | Shine (black) 20° | Shine (black) 60° |
|---|---|---|---|---|---|---|
| Comparative example 3 | Visionaire Sparkling Silver Sea | 2.00 | 42.0 | 92.1 | 40.0 | 89.3 |
| Example 3 | Visionaire Sparkling Silver Sea Ceraflour 913 | 2.00 5.00 | 2.3 | 5.5 | 2.1 | 5.7 |
| Example 4 | Visionaire Sparkling Silver Sea Ceraflour 913 | 2.00 10.00 | 1.4 | 2.8 | 0.8 | 2.1 |
| Example 5 | Visionaire Sparkling Silver Sea Ceraflour 913 | 2.00 15.00 | 1.2 | 2.3 | 0.8 | 1.9 |
| Example 6 | Visionaire Sparkling Silver Sea Ceraflour 913 | 2.00 20.00 | 1.2 | 2.3 | 0.9 | 2.0 |
| Example 7 | Visionaire Sparkling Silver Sea Ceraflour 914 | 2.00 5.00 | 3.0 | 7.0 | 3.2 | 8.1 |
| Example 8 | Visionaire Sparkling Silver Sea Ceraflour 914 | 2.00 10.00 | 1.4 | 2.7 | 0.8 | 2.0 |
| Example 9 | Visionaire Sparkling Silver Sea Ceraflour 914 | 2.00 15.00 | 1.3 | 2.6 | 0.8 | 2.1 |
| Example 10 | Visionaire Sparkling Silver Sea Ceraflour 914 | 2.00 20.00 | 1.2 | 2.9 | 1.0 | 2.7 |
| Comparative example 4 | Visionaire Sparkling Silver Sea Talc | 2.00 5.00 | 9.9 | 26.6 | 9.8 | 27.9 |
| Comparative example 5 | Visionaire Sparkling Silver Sea Talc | 2.00 10.00 | 4.5 | 11.6 | 4.2 | 11.2 |
| Comparative example 6 | Visionaire Sparkling Silver Sea Talc | 2.00 15.00 | 2.9 | 7.0 | 2.4 | 6.2 |
| Comparative example 7 | Visionaire Sparkling Silver Sea Talc | 2.00 20.00 | 2.1 | 4.8 | 1.8 | 4.5 |
| Comparative example 12 | Silverdream Polaris 90 WM | 2.00 | 16.4 | 58.9 | 17.1 | 60.2 |
| Example 20 | Silverdream Polaris 90 WM Ceraflour 913 | 2.00 5.00 | 0.9 | 2.7 | 1.2 | 4.0 |
| Example 24 | Silverdream Polaris 90 WM Ceraflour 914 | 2.00 5.00 | 1.1 | 3.4 | 1.2 | 4.0 |
| Example 25 | Silverdream Polaris 90 WM Ceraflour 914 | 2.00 10.00 | 0.5 | 1.0 | 0.4 | 0.9 |
| Example 26 | Silverdream Polaris 90 WM Ceraflour 914 | 2.00 15.00 | 0.4 | 0.8 | 0.2 | 0.6 |
| Example 27 | Silverdream Polaris 90 WM Ceraflour 914 | 2.00 20.00 | 0.4 | 0.9 | 0.2 | 0.8 |
| Comparative example 13 | Silverdream Polaris 90 WM Talc | 2.00 5.00 | 3.5 | 14.7 | 3.7 | 16.1 |
| Comparative example 14 | Silverdream Polaris 90 WM Talc | 2.00 10.00 | 1.6 | 6.1 | 1.6 | 6.3 |
| Comparative example 15 | Silverdream Polaris 90 WM Talc | 2.00 15.00 | 1.0 | 3.6 | 1.0 | 3.6 |
| Comparative example 16 | Silverdream Polaris 90 WM Talc | 2.00 20.00 | 0.7 | 2.3 | 0.7 | 2.3 |

IIIc Effect Measurements

Effect measurements for determining the optical influence of the at least one micronized wax were carried out by reference to nail varnish applications on black-white coverage cards (chart PA-2812, BYK-Gardner) using a BYK-mac (BYK-Gardner). Here, the nail varnishes were applied manually to the black-white coverage cards (wet film thickness 120 µm) using an Erichsen Film Applicator (System Wasag, model 288, Erichsen) and dried at room temperature. The nail varnishes selected by way of example have a different pigmentation level of effect pigment, different amounts of micronized waxes and also different micronized waxes. As reference, the nail varnish pigmented with the corresponding effect pigment was measured in each case without the addition of a micronized wax and with the addition of talc.

To simulate effect changes upon direct illumination, the glitter effect is investigated using the BYK-mac using a high-resolution CCD camera. The glitter effect, caused by the reflecting ability of the individual effect pigments, is only perceived upon direct solar irradiation and changes depending on the angle of illumination. For this reason, the sample is illuminated in the BYK-mac with very bright LEDs at three different angles (15°/45°/75°). The CCD camera is used here to take an image in each case perpendicularly to the surface. The images are analyzed using image processing algorithms, the histogram of the brightness stages being used as a basis for calculating the glitter parameters. In order to ensure better differentiation, the glitter effect was described by a two-dimensional system, the glitter area S_a and the glitter intensity S_i. Alternatively, said data were summarized by the one-dimensional value, the glitter degree S_G. The corresponding measurement values are summarized in Table 4. Here too, only phase A is mentioned; the commercially available nail varnish base International Lacquers Nailpolish & Care Base 359 (ad 100% by weight) was used as phase B.

TABLE 4

Glitter degree S_G, glitter intensity S_i and glitter area S_a

| Example/comparative example | Product name | % by weight | Measurement geometry (°) | S_G | S_i | S_a |
|---|---|---|---|---|---|---|
| Comparative example 1 | Visionaire Bright Silver Sea | 2.00 | 15 | 6.5 | 16.4 | 26.2 |
| | | | 45 | 4.7 | 12.0 | 20.5 |
| | | | 75 | 3.9 | 13.0 | 13.8 |
| Example 1 | Visionaire Bright Silver Sea | 2.00 | 15 | 6.5 | 14.4 | 30.5 |
| | Ceraflour 913 | 5.00 | 45 | 7.5 | 16.9 | 33.2 |
| | | | 75 | 9.3 | 28.0 | 29.9 |
| Example 2 | Visionaire Bright Silver Sea | 2.00 | 15 | 7.5 | 17.8 | 31.7 |
| | Ceraflour 914 | 5.00 | 45 | 8.5 | 22.2 | 31.7 |
| | | | 75 | 10.1 | 32.2 | 30.1 |
| Comparative example 2 | Visionaire Bright Silver Sea | 2.00 | 15 | 4.6 | 10.1 | 24.1 |
| | Talc | 20.00 | 45 | 5.4 | 11.5 | 27.4 |
| | | | 75 | 6.1 | 15.5 | 25.5 |
| Comparative example 3 | Visionaire Sparkling Silver Sea | 2.00 | 15 | 9.1 | 25.1 | 31.8 |
| | | | 45 | 4.1 | 9.9 | 19.6 |
| | | | 75 | 3.4 | 13.3 | 10.8 |
| Example 3 | Visionaire Sparkling Silver Sea | 2.00 | 15 | 8.8 | 21.6 | 34.6 |
| | Ceraflour 913 | 5.00 | 45 | 9.7 | 29.2 | 30.6 |
| | | | 75 | 10.5 | 40.8 | 25.4 |
| Example 4 | Visionaire Sparkling Silver Sea | 2.00 | 15 | 7.4 | 20.0 | 27.5 |
| | Ceraflour 913 | 10.00 | 45 | 7.8 | 21.8 | 28.0 |
| | | | 75 | 8.1 | 26.3 | 24.6 |
| Example 5 | Visionaire Sparkling Silver Sea | 2.00 | 15 | 7.4 | 20.0 | 27.3 |
| | Ceraflour 913 | 15.00 | 45 | 6.6 | 17.9 | 25.1 |
| | | | 75 | 6.1 | 21.0 | 18.6 |
| Example 6 | Visionaire Sparkling Silver Sea | 2.00 | 15 | 7.3 | 20.1 | 26.8 |
| | Ceraflour 913 | 20.00 | 45 | 6.2 | 20.2 | 19.6 |
| | | | 75 | 4.9 | 20.0 | 13.1 |
| Example 7 | Visionaire Sparkling Silver Sea | 2.00 | 15 | 11.0 | 33.8 | 33.6 |
| | Ceraflour 914 | 5.00 | 45 | 12.0 | 46.7 | 28.7 |
| | | | 75 | 12.2 | 58.3 | 23.6 |
| Example 8 | Visionaire Sparkling Silver Sea | 2.00 | 15 | 9.7 | 31.1 | 29.0 |
| | Ceraflour 914 | 10.00 | 45 | 9.6 | 33.3 | 26.2 |
| | | | 75 | 8.9 | 36.5 | 20.9 |
| Example 9 | Visionaire Sparkling Silver Sea | 2.00 | 15 | 10.3 | 34.8 | 28.7 |
| | Ceraflour 914 | 15.00 | 45 | 9.9 | 40.3 | 23.2 |
| | | | 75 | 7.7 | 33.6 | 17.5 |
| Example 10 | Visionaire Sparkling Silver Sea | 2.00 | 15 | 11.8 | 43.6 | 29.6 |
| | Ceraflour 914 | 20.00 | 45 | 10.8 | 52.0 | 21.2 |
| | | | 75 | 7.1 | 37.2 | 13.5 |
| Comparative example 4 | Visionaire Sparkling Silver Sea | 2.00 | 15 | 8.6 | 21.6 | 33.3 |
| | Talc | 5.00 | 45 | 7.3 | 20.3 | 26.4 |
| | | | 75 | 5.4 | 19.5 | 16.3 |
| Comparative example 5 | Visionaire Sparkling Silver Sea | 2.00 | 15 | 7.6 | 18.5 | 31.2 |
| | Talc | 10.00 | 45 | 7.3 | 18.6 | 29.1 |
| | | | 75 | 5.5 | 15.9 | 20.6 |
| Comparative example 6 | Visionaire Sparkling Silver Sea | 2.00 | 15 | 6.3 | 14.2 | 28.9 |
| | Talc | 15.00 | 45 | 6.5 | 15.1 | 28.8 |
| | | | 75 | 5.8 | 15.8 | 22.4 |
| Comparative example 7 | Visionaire Sparkling Silver Sea | 2.00 | 15 | 7.0 | 15.8 | 31.0 |
| | Talc | 20.00 | 45 | 6.5 | 14.7 | 29.8 |
| | | | 75 | 5.7 | 13.9 | 24.8 |
| Comparative example 8 | Visionaire Sparkling Silver Sea | 1.00 | 15 | 10.0 | 28.9 | 32.8 |
| | Mirage Glamour Red | 1.00 | 45 | 5.0 | 15.4 | 18.1 |
| | | | 75 | 4.0 | 17.3 | 10.9 |
| Example 16 | Visionaire Sparkling Silver Sea | 1.00 | 15 | 9.4 | 23.8 | 35.3 |
| | Mirage Glamour Red | 1.00 | 45 | 9.9 | 29.8 | 31.5 |
| | Ceraflour 913 | 5.00 | 75 | 10.3 | 42.5 | 23.7 |
| Example 17 | Visionaire Sparkling Silver Sea | 1.00 | 15 | 11.0 | 32.9 | 34.7 |
| | Mirage Glamour Red | 1.00 | 45 | 11.7 | 44.7 | 28.3 |
| | Ceraflour 914 | 5.00 | 75 | 11.2 | 60.2 | 19.4 |
| Comparative example 9 | Visionaire Sparkling Silver Sea | 1.00 | 15 | 6.3 | 13.8 | 29.8 |
| | Mirage Glamour Red | 1.00 | 45 | 6.7 | 16.1 | 28.4 |
| | Talc | 20.00 | 75 | 5.5 | 14.7 | 21.7 |
| Comparative example 10 | Silverdream Moonlight 50IL | 2.00 | 15 | 1.6 | 5.5 | 8.8 |
| | | | 45 | 3.1 | 7.0 | 17.6 |
| | | | 75 | 3.6 | 13.9 | 11.3 |
| Example 18 | Silverdream Moonlight 50IL | 2.00 | 15 | 3.2 | 6.0 | 21.9 |
| | Ceraflour 913 | 5.00 | 45 | 4.0 | 6.7 | 27.7 |
| | | | 75 | 6.4 | 12.3 | 34.6 |
| Example 19 | Silverdream Moonlight 50IL | 2.00 | 15 | 4.1 | 8.0 | 24.6 |
| | Ceraflour 914 | 5.00 | 45 | 4.8 | 8.2 | 31.0 |
| | | | 75 | 7.3 | 14.8 | 36.2 |
| Comparative example 11 | Silverdream Moonlight 50IL | 2.00 | 15 | 2.4 | 5.0 | 16.8 |
| | Talc | 20.00 | 45 | 3.6 | 6.5 | 24.5 |
| | | | 75 | 5.6 | 11.3 | 29.8 |

TABLE 4-continued

Glitter degree S_G, glitter intensity S_i and glitter area S_a

| Example/comparative example | Product name | % by weight | Measurement geometry (°) | S_G | S_i | S_a |
|---|---|---|---|---|---|---|
| Comparative example 21 | SynCrystal Silver | 2.00 | 15 | 3.8 | 8.4 | 20.5 |
| | | | 45 | 1.2 | 3.7 | 8.7 |
| | | | 75 | 1.1 | 6.5 | 4.7 |
| Example 38 | SynCrystal Silver | 2.00 | 15 | 5.0 | 9.3 | 30.0 |
| | Ceraflour 913 | 5.00 | 45 | 6.1 | 12.1 | 32.0 |
| | | | 75 | 7.4 | 19.0 | 29.0 |
| Example 39 | SynCrystal Silver | 2.00 | 15 | 5.9 | 11.5 | 32.0 |
| | Ceraflour 914 | 5.00 | 45 | 7.2 | 16.1 | 32.1 |
| | | | 75 | 8.2 | 24.2 | 27.5 |
| Comparative example 22 | SynCrystal Silver | 2.00 | 15 | 3.8 | 7.5 | 23.2 |
| | Talc | 20.00 | 45 | 4.2 | 8.2 | 24.9 |
| | | | 75 | 4.6 | 10.8 | 22.0 |
| Comparative example 23 | SynCrystal Sparkling Silver | 2.00 | 15 | 6.5 | 16.7 | 25.4 |
| | | | 45 | 2.2 | 5.5 | 13.2 |
| | | | 75 | 1.9 | 9.1 | 6.5 |
| Example 40 | SynCrystal Sparkling Silver | 2.00 | 15 | 8.2 | 19.0 | 34.5 |
| | Ceraflour 913 | 5.00 | 45 | 8.3 | 23.0 | 29.2 |
| | | | 75 | 8.4 | 28.6 | 23.9 |
| Example 41 | SynCrystal Sparkling Silver | 2.00 | 15 | 10.0 | 27.8 | 34.2 |
| | Ceraflour 914 | 5.00 | 45 | 9.7 | 30.7 | 29.0 |
| | | | 75 | 9.1 | 38.8 | 20.5 |
| Comparative example 24 | SynCrystal Sparkling Silver | 2.00 | 15 | 5.8 | 12.8 | 27.9 |
| | Talc | 20.00 | 45 | 5.1 | 12.2 | 23.8 |
| | | | 75 | 3.9 | 10.6 | 16.8 |
| Comparative example 27 | Mirage Bright Blue | 2.00 | 15 | 6.8 | 16.6 | 28.6 |
| | | | 45 | 2.7 | 4.1 | 24.2 |
| | | | 75 | 1.8 | 5.4 | 10.1 |
| Example 53 | Mirage Bright Blue | 2.00 | 15 | 5.5 | 12.3 | 26.5 |
| | Ceraflour 913 | 5.00 | 45 | 5.7 | 15.3 | 22.5 |
| | | | 75 | 4.7 | 14.3 | 17.3 |
| Example 54 | Mirage Bright Blue | 2.00 | 15 | 6.7 | 18.5 | 24.7 |
| | Ceraflour 914 | 5.00 | 45 | 6.2 | 18.8 | 21.2 |
| | | | 75 | 5.2 | 16.5 | 17.9 |
| Comparative example 28 | Mirage Bright Blue | 2.00 | 15 | 3.4 | 6.5 | 22.5 |
| | Talc | 20.00 | 45 | 2.8 | 5.3 | 19.6 |
| | | | 75 | 2.2 | 5.5 | 13.6 |

The one-dimensional glitter degree S_G is decisive for the optical impression. The higher the numerical value of S_G, the higher the glitter effect that can be perceived even by the eye. In a two-dimensional representation, the glitter degree S_G can be divided into the components glitter intensity S_i and glitter area S_a. Since both components have a decisive influence on the glitter degree S_G, what can occur is that an effect pigment in the measurement geometries 15°, 45° and 75° has virtually the same glitter degree S_G although the numerical values of S_a and S_i in the observed measurement geometries are significantly increased or reduced. Thus, e.g. a nail varnish application of 2% by weight of Visionaire Sparkling Silver Sea and 5% by weight of Ceraflour 913 (example 3) at 15° measurement geometry had a glitter degree S_G of 8.8, the glitter intensity S_i being 21.6 and the glitter area S_a being 34.6. At 75°, a glitter degree S_G of 10.5 was ascertained, i.e. the perceptible glitter effect had changed little. Nevertheless, the components glitter intensity S_i and glitter area S_a changed significantly—the glitter intensity S_i increased to 41, the glitter area S_a dropped to 25. The reduced glitter area S_a was thus completely compensated by the considerably increased glitter intensity, meaning that only an insignificant change in the glitter effect was perceived by the viewer.

IV Characterization of the Optical and Haptic Effects of the Nail Varnishes According to the Invention IVa Scanning Electron Micrographs of the Nail Varnishes The scanning electron micrographs (FIGS. 5 to 9) were obtained using transverse sections of the nail varnishes according to the invention with the Supra 35 scanning electron microscope (Zeiss).

IVb Light-Microscopic Depth Profiles of the Nail Varnishes

The depth profiles were established with the help of light micrographs of nail varnish applications on black-white coverage cards (chart PA-2812, BYK-Gardner) using the Axio Imager.Zlm microscope (Zeiss). Here, the nail varnishes were applied manually to the black-white coverage cards (wet film thickness 120 μm) using an Erichsen Film Applicator (System Wasag, model 288, Erichsen) and dried at room temperature.

By way of example, nail varnishes were measured which were provided with an effect pigment, without micronized wax, different micronized waxes and also with talc (Table 5).

TABLE 5

Composition of the nail varnishes (phase A) for microscopic depth profiles, phase B corresponds to that described above

| Example/comparative example | Product name | % by weight |
|---|---|---|
| Comparative example 3 | Visionaire Sparkling Silver Sea | 2.00 |
| Example 3 | Visionaire Sparkling Silver Sea | 2.00 |
| | Ceraflour 913 | 5.00 |
| Example 7 | Visionaire Sparkling Silver Sea | 2.00 |
| | Ceraflour 914 | 5.00 |
| Comparative example 7 | Visionaire Sparkling Silver Sea | 2.00 |
| | Talc | 20.00 |

In each case two microscope images were taken per micrometer of the nail varnish application over a height range of ca. 30 μm perpendicular to the black-white coverage card;

these were then superimposed using the image processing software AxioVision 4.6.3. to give a single microscope image (FIGS. 10 to 13) and at the same time recalculated to give a topography image. The surface parameter "roughness value" Rq was calculated from this topography image in accordance with DIN EN ISO 4287:2010-07. An identically pigmented nail varnish without the addition of micronized wax was used for the comparison. The roughness values of the nail varnishes described in Table 5 are shown in FIG. 14. A comparison of the roughness values demonstrated the haptically feelable influence of a micronized wax. A nail varnish which comprises exclusively an effect pigment was characterized by its comparatively smooth surface, which was also reflected in the associated topography image and correspondingly low roughness value. The addition of at least one micronized wax had a clear effect on the topography image, the hill and valley structure was more pronounced, the associated roughness values increased very considerably compared to a nail varnish without micronized wax. This influence could also be detected in terms of feel. A comparable haptic effect and comparable roughness values were only observed for a considerably increased talc content.

The invention claimed is:

1. A nail varnish having a velvety feel, the nail varnish comprising:
   (1) at least one effect pigment in a range from 0.05 to 6.0% by weight, based on the total weight of the nail varnish, wherein the at least one effect pigment has an average particle size $D_{50}$ of the cumulative frequency distribution of the volume-averaged size distribution function from a range from 1 to 100 μm; and
   (2) at least one micronized wax in a range from 1 to 15% by weight, based on the total weight of the nail varnish, wherein the at least one micronized wax has an average particle size $D_{50}$ of the cumulative frequency distribution of the volume-averaged size distribution function from a range from 2.5 to 91 μm,
   wherein a ratio of the average particle size $D_{50}$ of the at least one effect pigment to the average particle size $D_{50}$ of the at least one micronized wax according to the formula (I)

$$\frac{D_{50} \text{ effect pigment}}{D_{50} \text{ micronized wax}} \quad (I)$$

is in a range from 0.1 to 12.0,
   wherein the nail varnish has a light/dark flop index of 8.2 or less, and
   wherein the nail varnish has a roughness value $R_q$ greater thean the roughness value of the nail varnish without the at least one micronized wax.

2. The nail varnish according to claim 1, wherein the at least one effect pigment comprises a metal effect pigment, a pearlescent pigment, or a combination of metal effect pigment and pearlescent pigment.

3. The nail varnish according to claim 1, wherein the at least one micronized wax comprises a natural wax, a synthetic wax, or a combination of natural and synthetic waxes.

4. The nail varnish according to claim 1, wherein the at least one micronized wax is a synthetic uncolored wax.

5. The nail varnish according to claim 1, wherein the nail varnish comprises a mixture with at least one effect pigment and at least one micronized wax in a ratio of 10 to 49% by weight of effect pigment to 51 to 90% by weight of micronized wax, based on the total weight of the components effect pigment and micronized wax.

6. A process for producing a nail varnish having a velvety feel according to claim 1, wherein the process comprises at least the following step:
   combining a nail varnish base, at least one micronized wax in a range from 1 to 15% by weight, based on the total weight of the nail varnish, and at least one effect pigment in a range from 0.05 to 6.0% by weight, based on the total weight of the nail varnish, to prepare a nail varnish, wherein the at least one effect pigment has an average particle size $D_{50}$ of the cumulative frequency distribution of the volume-averaged size distribution function from a range from 1 to 100 μm, wherein the at least one micronized wax has an average particle size $D_{50}$ of the cumulative frequency distribution of the volume-averaged size distribution function from a range from 2.5 to 91 μm,
   wherein a ratio of the average particle size $D_{50}$ of the at least one effect pigment to the average particle size $D_{50}$ of the at least one micronized wax according to the formula (I)

$$\frac{D_{50} \text{ effect pigment}}{D_{50} \text{ micronized wax}} \quad (I)$$

is in a range from 0.1 to 12.0,
   wherein the nail varnish has a light/dark flop index of 8.2 or less, and
   wherein the nail varnish has a roughness value $R_q$ greater thean the roughness value of the nail varnish without the at least one micronized wax.

7. An article comprising the nail varnish according to claim 1.

8. The article according to claim 7, further comprising an artificial fingernail.

9. The article according to claim 8, wherein the nail varnish is applied to the artificial fingernail.

10. The article according to claim 9, wherein the nail varnish is applied in a single layer to the artificial fingernail.

11. A process for producing an artificial nail, comprising:
   applying a nail varnish according to claim 1 to an artificial nail.

* * * * *

UNITED STATES PATENT AND TRADEMARK OFFICE
CERTIFICATE OF CORRECTION

| | |
|---|---|
| PATENT NO. | : 8,889,107 B2 |
| APPLICATION NO. | : 13/575153 |
| DATED | : November 18, 2014 |
| INVENTOR(S) | : Ulrich Schmidt et al. |

It is certified that error appears in the above-identified patent and that said Letters Patent is hereby corrected as shown below:

In the Claims

Column 47, Line 51, Claim 1, delete "thean" and insert -- than --

Column 48, Line 41, Claim 6, delete "thean" and insert -- than --

Signed and Sealed this
Seventeenth Day of March, 2015

Michelle K. Lee
*Director of the United States Patent and Trademark Office*